United States Patent
Schoonjans et al.

(10) Patent No.: US 6,809,185 B1
(45) Date of Patent: Oct. 26, 2004

(54) MULTIPURPOSE ANTIBODY DERIVATIVES

(75) Inventors: Reinhilde Schoonjans, Landegem (BE); Nico Mertens, Melsele (BE); Walter Fiers, Destelbergen (BE); Roland Contreras, Schelderode-Merelbeke (BE)

(73) Assignee: Vlaams Interuniversitair Instituut Voor Biotechnologie, Zwinjnaarde (BE)

( * ) Notice: Subject to any disclaimer, the term of this patent is extended or adjusted under 35 U.S.C. 154(b) by 0 days.

(21) Appl. No.: 09/625,049

(22) Filed: Jul. 24, 2000

Related U.S. Application Data

(63) Continuation of application No. PCT/EP99/00477, filed on Jan. 25, 1999, now abandoned.

(30) Foreign Application Priority Data

Jan. 23, 1998 (EP) ............................................. 98200193

(51) Int. Cl.$^7$ ............................................. C07K 16/00
(52) U.S. Cl. ................................ 530/387.3; 530/387.1; 530/388.1
(58) Field of Search .......................... 530/387.1, 387.3, 530/388.1, 391.5; 435/188; 424/130.1, 133.1, 135.1, 136.1

(56) References Cited

U.S. PATENT DOCUMENTS 5,648,237 A * 7/1997 Carter

FOREIGN PATENT DOCUMENTS

| WO | WO 94/09131 | * | 4/1994 |
| WO | WO 99/37791 | * | 7/1999 |

OTHER PUBLICATIONS

Muller et al., FEBS Letters 422259–64, 1998.*
Tutt et al., The journal of Immunology 147:60–69, 1991.*
Chester et al., TIBTECH 13:296, 1995.*
Huston et al., Methods in Enzymology 203:46–88, 1991.*
Paul, Fundamental immunology, Raven Press, p. 299–300, 1993.*
Hennie R. Hoogenboom, *Mix and match: Building manifold binding sites*, Nature Biotechnology, vol. 15, Feb. 1997, pp. 125–126.
H. Perry Fell et al., *Genetic Construction and Characterization of a Fusion Protein Consisting of a Chimeric F(ab') with Specificity for Carcinomas and Human IL–2*, The Journal of Immunology, vol. 146, No. 7, Apr. 1, 1991, pp. 2446–2452.
F. Duncancel et al., *Genetically engineered colorimetric antibody*, Protein Enginnering, vol. 6, No. Suppl., 1993, p. 87.
Eini Nyyssönen et al., *Efficient Production of Antibody Fragments by the Filamentous Fungus Trichoderma reesei*, Bio/Technology, vol. 11, May 1993, pp. 591–595.
Mark A. Nedelman et al., *Rapid Infarct Imaging with a Technetium–99m–Labeled Antimyosin Recombinant Single–Chain Fv: Evaluation in a Canine Model of Acute Myocardial Infarction*, The Journal of Nuclear Medicine, vol. 34, No. 2, Feb. 1993, pp. 234–241.
D.C. Anderson et al., *Enhanced in Vitro Tumor Cell Retention and Internalization of Antibody Derivatized with Synthetic Peptides*, Bioconjugate Chem., vol. 4, 1993, pp. 10–18.

* cited by examiner

Primary Examiner—Larry R. Helms
(74) Attorney, Agent, or Firm—Knobbe, Martens, Olson & Bear, LLP

(57) ABSTRACT

The present invention relates to a class of molecules specified as novel multipurpose antibody derivatives. This class of molecules is created by heterodimerization of two constituting components. Heterodimerization is obtained by the specific heterotypic interaction of a chosen VH-CH1 combination of immunoglobulin domains, with a chosen VL-CL combination of immunoglobulin domains. The appropriate VH and VL domains in the VHCH1 and VLCL context, a binding specificity can be constitituted by the heterodimerization scaffold itself. One or both of the comprising VHCH1 and VLCL chains can thus be extended at either the N- or the C-terminus or both with other molecules, such as a toxin polypeptide, an enzyme, a hormone, a cytokine, a signaling molecule, or a single chain linked Fv fragment with the same or a different specificity.

16 Claims, 14 Drawing Sheets

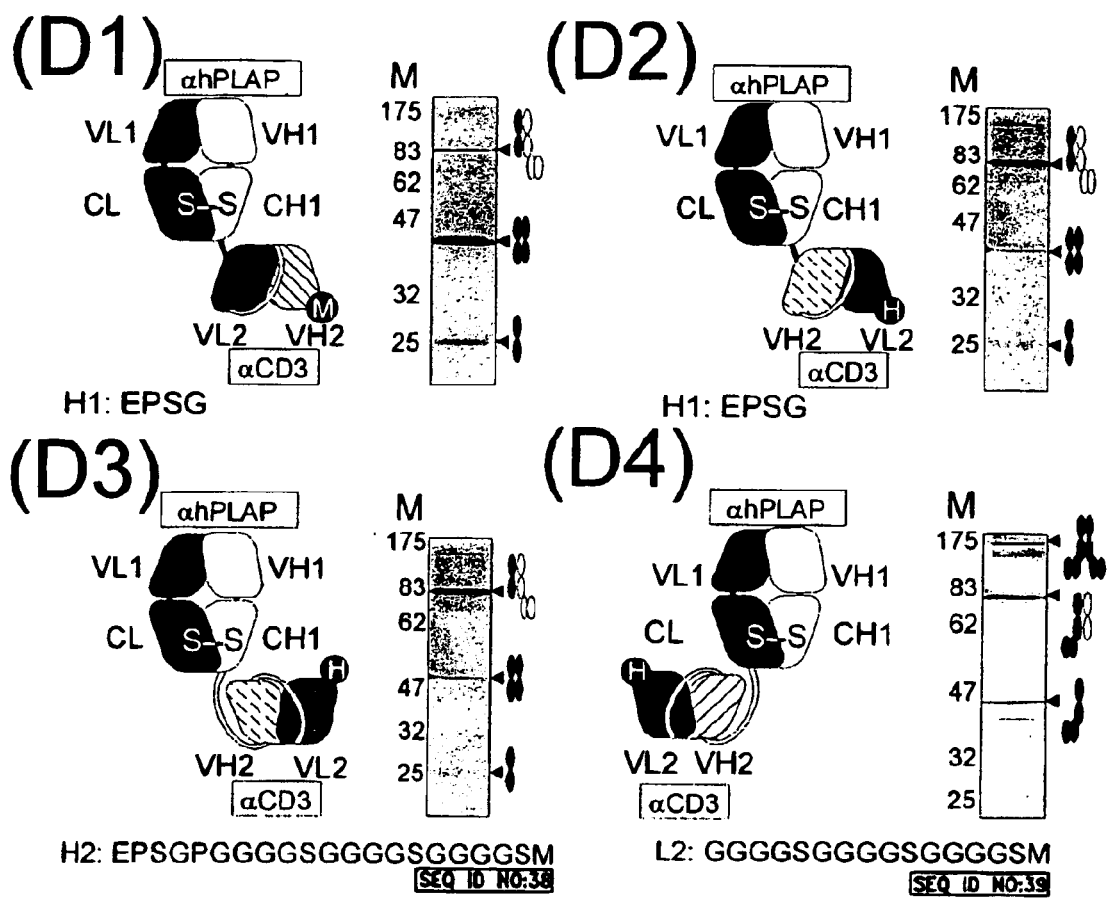

MULTIPURPOSE ANTIBODY DERIVATIVES

This is a continuation of International Application PCT/EP99/00447, with an international filing date of Jan. 25, 1999, published in English under PCT Article 21(2) and now abandoned.

TECHNICAL FIELD

The present invention relates to a class of molecules specified as novel multipurpose antibody derivatives. The invention further relates in particular to such antibody derivatives that have two or more antigen binding parts, derivatives that have at least two antigen binding parts, combined with at least one other function, such as a toxin, an enzyme, a cytokine, a hormone or a signalling molecule, and derivatives that have an antigen binding part, combined with at least two other functions.

BACKGROUND OF THE INVENTION

Due to their versatility, multipurpose antibody derivatives (mpAbs), such as bispecific antibodies (BsAb), immunotoxins and bifunctional antibodies are promising tools in the treatment of various (human) diseases. The first arm usually allows to specifically recognize a target cell (e.g. cancer cell) by means of an antigen binding function, while another determinant may be directed through an antigen binding function towards a second cell type (e.g. a cytotoxic T cell), or it may be a toxin, an enzyme (e.g. to locally cleave and activate a prodrug), a cytokine, a hormone or a signalling molecule.

The difficulty of producing functional BsAb in sufficient quantity and purity is still hampering the more general use of BsAb in clinical applications. When using the guadroma technology only 10% of the immunoglobulin pool is the correct, bispecific antibody. Therefore, time consuming and costly purification procedures are inevitable.

Chemical reassociation of antibody fragments suffers from loss of affinity by protein denaturation or unorthodox disulphide bond formation, as well as from the use of a chemical cross-linker, generating inactive, chemically modified structures.

Both these classical methods producing BsAb give rather low yields. Recombinant DNA methodology and antibody engineering has greatly facilitated the production of antibody derivatives in heterologous expression systems. By genetic fusion of various antibody fragments to generate BsAb, the normal tetrameric antibody structure $(H+L)_2$ is reduced. When the total Fc-portion is included, the self-association of the disulphide bridges in the hinge region reduces considerably the yield of heterodimeric BsAb. Hence purification away from bivalent, homodimeric by-products is still required. In order to improve the level of heterodimeric, bispecific product, a "Knobs-into-holes" principle has been developed to engineer the CH3 domains in the Fc-tail for preferential heterodimerization. The molecule proposed by Ridgway et al. (1996) comprises a complete Fc portion, which increases the molecular weight of the final protein beyond the optimal size for biodistribution. Furthermore, the Fc portion can interact with a multitude of Fc receptors present on various cells in the body, which can deviate the binding of this molecule to aspecific targets.

Small antibody-derivatives (such as sFv, bssFv, (diabodies) have the advantage of easy penetration in solid tumors; moreover, partly because of the absence of high disulphide containing hinge regions, they can be produced in high amounts in heterologous expression systems. However, due to their small size, these molecules are generally cleared too rapidly from the circulation to allow efficient accumulation at the tumor site, while molecules of intermediate size have improved serum stability and retain satisfactory tissue penetration.

In order to achieve medium sized heterodimers, sFv have been linked by incorporating an additional peptide, leucine zippers, amphiphatic helices or streptavidin. These heterodimerization extensions, however, might be immunogenic.

Similar problems are encountered in the preparation of immunotoxins and antibody derivatives having an enzymatic function. Monovalent single chain Fv fragments (sFv) or disulfide stabilized Fv fragments (dsFv) are predominantly used to construct toxin fusions. This results in weaker binding and poor internalization due to the monovalent binding, and rapid blood clearance due to the small molecule size.

DISCLOSURE OF INVENTION

In view of the above it is the object of the present invention to provide a class of molecules, specified as novel multipurpose antibody derivatives that can be efficiently prepared without many by-products, that have an intermediate size and that combine two or more antigenic binding sites, or one antigenic binding site with two or more other functions in one molecule.

This is achieved according to the invention by multipurpose antibody derivative, comprising the CL and VL domains of a first antibody with a desired first antigen binding specificity, the CH1 and VH domains of the said first antibody interacting with the CL and VL domains, and one or more other molecules having at least one further purpose coupled to one or more of the domains of the first antibody.

The invention is based on the potential of the specific VL-CL:VH-CH1 (referred to as "L:Fd") interaction to drive disulphide-stabilized heterodimerization of recombinant antibody-derived fusion proteins. The use of the L:Fd interaction which can be both natural or chimeric to drive heterodimerization has several advantages. First of all, their natural heterodimeric interaction circumvents the need for protein engineering to achieve complementarity. Furthermore, the interaction is very strong, in contrast to L:L homodiners which are only poorly formed or Fd:Fd homodimers which were never detected in eukaryotic expression systems. Also, in bacterial expression systems the Fd chain alone is aberrantly folded (Ward, 1992). Finally, a single, natural disulphide bridge stabilizes the L:Fd heterodimer.

Each of the two domains of the light and heavy chain can be extended with another molecule (e.g. VL or VH region, a sFv, a toxin, an enzyme such as a prodrug cleaving enzyme, a cytokine, a hormone, a signalling molecule, etc.).

Thus, the invention relates to a class of molecules specified herein as novel "multipurpose antibody derivatives". This class of molecules is created by heterodimerization of two constituting components. Heterodimerization is obtained by the specific heterotypic interaction of a chosen CH1-VH combination of immunoglobulin domains, with a chosen CL-VL combination of immunoglobulin domains. The VHCH1-VLCL interaction is proposed as a very efficient heterodimerization scaffold that could be efficiently produced. By choosing the tappropriate VH and VL domains in the VHCH1 and VLCL context, a binding specificity can be constituted by the heterodimerization scaffold itself. One or both of the comprising VHCH1 and VLCL chains can thus be extended at either the N- or the C-terminus or both with other molecules, such as a toxin, an enzyme, a cytokine, a hormone or a signalling molecule and derivatives that have an antigen binding part for the purpose of combining these molecules with each other.

The construction of the Fab part of the antibody, fixed to relatively simple molecules such as bacterial alkaline phosphatase, or a truncated mutant form of Pseudomonas exotoxin has been described before (Ducancel et al., 1993, Choe et al., 1994). However, unexpectedly it was found according to the invention that the L:Fd interaction is still able to drive the heterodimerization when one of the chains of the Fab is fused to a complex molecule as a single-chain antibody fragment. Even more unexpectedly, it was found that also both chains of the Fab may be fused to other molecules, without affecting the ability of the molecules to form preferentially heterodimers.

ScFv molecules consist of domains (VL and VH) of the same nature as can be found in the Fd and L chains, so wrongly formed non-functional derivatives could easily be expected. However, the findings as illustrated in the examples unexpectedly show that such molecules can be produced efficiently and is proven functional for all its components.

Surprisingly, this could be achieved with peptide linkers as short as a few amino acids. By excluding the hinge-region, dimerization of the Fab-scFv fusion is omitted. Homodimerization of some specificities might induce unwanted activating or inhibiting functions with effector cells. In order to avoid this, homodimerization through e.g. the hinge region can be avoided by excluding this region in the Fab-scFv molecule.

The other molecule(s) can be fused either to the C-terminus of the CH1 the N-terminus of the VH, the C-terminus of the CL and/or the N-terminus of the VL. In total, the invention offers 15 different variant types of combinations of other molecules with the L+Fd construct as a scaffold. The variant types are summarized in table 1. Each variant type can in turn be provided with various kinds of other molecules.

TABLE 1

| No. | other molecule on C-terminus $CH_1$ | other molecule on H-terminus VH | other molecule on C-terminus CL | other molecule on W-terminus VL |
|---|---|---|---|---|
| 1 | + | − | − | − |
| 2 | − | + | − | − |
| 3 | − | − | + | − |
| 4 | − | − | − | + |
| 5 | + | + | − | − |
| 6 | − | + | + | − |
| 7 | − | − | + | + |
| 8 | + | − | − | + |
| 9 | + | − | + | − |
| 10 | − | + | − | + |
| 11 | + | + | + | − |
| 12 | + | + | − | + |
| 13 | + | − | + | + |
| 14 | − | + | + | + |
| 15 | + | + | + | + |

The L:Fd acts as a "carrier" for the other molecule. In the case of an sFv as the other molecule, the total size of the sFv is increased due to the presence of the carrier. As a consequence it will not have the disadvantage of known sFv's or bssFv that are cleared too rapidly from the circulation. The L and Fd chains can if desired, constitute a binding specificity of their own. In this case, the L and Fd chains contribute a function of their own, apart from serving as a heterodimerization signal.

When a molecule of the invention combines two (different of equal) functions, it is called bifunctional. Similarly, when a molecule of the invention combines three or more than three different or equal functions, it is called trifunctional, respectively multifunctional. When a molecule of the invention is combining two, three or more antibody parts having a different specificity, it is called bi-, respectively tri- or multispecific. When a molecule of the invention is combining two, three or more antibody parts having the same specificity, it is called bi-, respectively, tri- or multivalent for the binding specificity.

In a first preferred embodiment, the invention provides for a novel, recombinant mpAB that is a bispecific, bifunctional antibody (BsAb) when the specificities are different or bivalent, bifunctional antibody (BvAb) when the specificities are the same. These are based on the fusion of a Fab and a sFv, which is fused to the C-terminus of CH1 or CL. This molecule will have an intermediate size of about 80 kDa, satisfies the aforementioned criteria and incorporates preferential heterodimerization through its L:Fd domains.

According to a second preferred embodiment a similar antibody is provided which is also based on the fusion of a Fab and a sFv, but in this case the latter is fused to the N-terminus of VH or the N-terminus of VL. In a third preferred embodiment, the invention provides for a novel, recombinant bispecific, trifunctional or bivalent, trifunctional mpAB that is an immunotoxin based on the fusion of a BsAb or a BvAb according to the first embodiment and a toxin, which is fused to the C-terminus of the heavy chain of the Fab that does not carry the sFv.

According to a fourth preferred embodiment, the invention provides for a novel, recombinant bispecific, trifunctional or bivalent, trifunctional mpAB that is called a catalytic antibody (cAb) based on the fusion of a BsAb or a BvAb and an enzyme, which is fused to the C-terminus of the heavy chain of the Fab that does not carry the sFv.

According to a fifth preferred embodiment, the invention provides for a novel, recombinant bispecific, trifunctional or bivalent, trifunctional mpAB that is combined with a hormone, a cytokine or a signalling function by fusing of a molecule with said activity to an BsAb or a BvAb according to the first embodiment.

According to a sixth preferred embodiment both the C-terminus of CH1 and the C-terminus of CL are fused to a sFv, resulting in a molecule with three antigen binding parts. This molecule is trifunctional, and can be trivalent monospecific, bivalent bispecific or monovalent trispecific.

Thus, this invention offers inter alia the possibility to create bivalent trifunctional immunotoxins (i.e. molecules that are intended for two purposes, namely bivalent antigen binding and toxicity) or trispecific (i.e. three antigen specificities), antibodies. In the latter case not only the CH1, but also the CL is extended with an sFv.

The other molecule can be linked to the L or Fd antibody part(s) directly or via a linker. The presence of a linker of at least 1, preferably more than 3 amino acids can be used to avoid steric hindrance between two or more antigen binding sites and between antigen binding site(s) and the active center of the other molecule. Linkers other than amino acid chains may also be used.

According to one specifically preferred embodiment of the invention various anti murine CD3ε-single-chain fragments (sFv) were fused to the C-terminus of CH1 of an Fd fragment specific for human placental alkaline phosphatase (hPLAP). This Fab-sFv bispecific antibody derivative (of the general formula Fab-linker-sFv, wherein the linker is e.g. EPSG but can be variable in sequence and length) can be used to link cytotoxic cells to tumor cells.

The fusion product was further improved for reaching far apart antigens by providing a sufficiently long spacer sequence (of the general formula Fab-linker-sFv, wherein the linker is e.g. EPSGP$(G_4S)_3$M but can be variable in sequence and length). After eukaryotic secretion, specific heterodimerization between the corresponding anti-hPLAP light chain and the Fd fragment occurred, where the latter carried a functional sFv. Upon expression in mammalian cells more than 90% of the immunoglobulin material in the medium was the specific heterodimer, with only minor contamination of light chain derived homodimers and monomers, which did not show hPLAP binding capacity. Homodimers from the heavy chain derived VH-CH1 fused to the anti CD3ε sFv were never observed.

The Fab-sFv fusion protein between the anti murine CD3ε sFv and the anti-hPLAP-Fab here described is an example for the efficient production of specific, disulphide stabilized heterodimers which can be used for making bispecific antibodies. The invention is not limited to this particular example. Other antigen binding specificities can be used and for the other purpose or function there is also a variety of options. The invention lies in principle in the finding that the L:Fd interaction is highly specific and can be used as a heterodimeric scaffold to construct a new type of mpAb. The VL and CL domains in the L chain, as well as the Vh and CH1 domains in the Fd chain do not necessarily have to be derived from the same antibody.

The derivatives of the invention can, be used in the treatment of tumors, in the treatment of various infected cells, in the treatment of autoimmune diseases or thrombosis. Moreover the derivatives of the invention can be used to direct a virus towards immunological effector cells, to induce or resolve blood clotting, to eliminate specific cell types in vitro or in vivo, to establish or improve transfections, or in diagnosis.

The invention further relates to DNA constructs encoding the heavy chain domains of an antibody derivative of the invention, comprising suitable transcription and translation regulatory sequences operably linked to sequences encoding the VH and CH1 domains of the first antibody and optionally a coding sequence for the other molecule operably linked thereto.

In such a DNA construct the coding sequence for the other molecule may consist of DNA sequences encoding the VL and VH domains of a second antibody, which DNA sequences are operably linked to each other in either one of the sequences 5'-VL2-VH2-3' or 5'-VH2-VL2-3'.

In the DNA construct a DNA sequence encoding a linker sequence may be incorporated between one or more of the VH, CH1, VL2 and/or VH2 coding sequences and/or the coding sequence for the other molecule. The linker helps in avoiding steric hindrance between the various domains.

A particularly preferred DNA construct, designated as pCA2C11sFvE6Hf, is obtainable from *E. coli* DH5α cells deposited on Oct. 15, 1997 at the Belgian Coordinated Collection of Microorganisms and given the deposit accession no. LMBP3715. Another preferred DNA construct is designated as pCAE6HfGS2C11sFv (also identified as pCAE6H2sc2C11H) and obtainable from *E. coli* MC1061 cells deposited on Oct. 15, 1997 at the Belgian Coordinated Collection of Microorganisms and given the deposit accession no. LMBP3716.

Furthermore the invention relates to DNA construct encoding the light chain domains of an antibody derivative of the invention, comprising suitable transcription and translation regulatory sequences operably linked to sequences encoding the VL and CL domains of the first antibody and optionally a coding sequence for the other molecule operably linked thereto. The coding sequence for the other molecule may consist of DNA sequences encoding the VL and VH domains of a second antibody, which DNA sequences are operably linked to each other in either one of the sequences 5'-VL2-VH2-3' or 5'-VH2-VL2-3'.

Also in this DNA construct a linker sequence can be incorporated between one or more of the VL, CL, VL2 and/or VH2 coding sequences and/or the coding sequence for the other molecule.

According to a further aspect the invention relates to a set of DNA constructs for producing multipurpose antibody derivatives of the invention, comprising any one of the constructs described above together with a construct encoding at least the light domains VL and CL of the first antibody or together with a construct encoding at least the heavy domains VH and CH of the first antibody, depending on whether the other construct encodes the heavy or light domains of the first antibody.

In a first embodiment the set consists of vector pCAE6H2sc2C11H and vector pCAG6SE6L. In an alternative embodiment the set consists of vector pCA2C11sFvE6Hf and vector pCAG6SE6L. Those sets can be used for producing multipurpose antibody derivatives of the invention in heterologous expression host cells. The invention also relates to a method for producing multipurpose antibody derivatives, comprising expression of such a set in heterologous expression host cells. The host cells may be *E. coli* cells, other bacterial cells, such as Bacillus spp., Lactobacillus spp. or Lactococcus spp.; actinomycetes; yeasts; filamentous fungi; mammalian cells, such as COS-1 cells, HEK cells, insect cells, transgenic animals or plants.

Another aspect of the invention relates to a medical preparation, comprising multipurpose antibody derivatives.

A further aspect of the invention relates to the use of multipurpose antibody derivatives in diagnosis.

According to a final aspect the invention relates to the use of multipurpose antibody derivatives for the preparation of a medicament for the treatment of cancer, infections, parasites, autoimmune diseases, thrombosis.

The term "purpose" is used herein to indicate a certain activity or other function, preferably antigen binding specificity, toxicity, signalling or enzymatic activity.

The term "derivative" is used herein to refer to molecules other than the classic antibodies consisting of two light chains and two heavy chains, which heavy chains in turn comprise multiple constant domains. The derivatives comprise at least one VL domain, one CL domain, one VH domain and one CH domain.

Derivatives of the present invention can thus be prepared by genetic engineering using methods well known in the art. In the examples that follow, it is described how by genetic engineering, a new type of bispecific antibody with potential use in immunotherapy by redirected cellular cytotoxicity was designed. The design of the antibody was bas d on the very effective and selective heterodimerization of the two antibody-chains, L and Fd. Both the Fd and the L chain can be extended with new determinants, herein called "other molecules" (peptides, domains), either at their N-terminus or C-terminus or both. As an example the molecule Fab (L+Fd) is described extended either at the N-terminus or at the C-terminus of the Fd fragment with a single chain antibody fragment (sFv). The latter, Fab-(G$_4$S)$_3$-sFv, was characterized in detail. (G4S)$_3$ is short for EPSG-PGGGGSGGGGSGGGGSM (SEQ ID NO:30). The bispecific species was the predominant product in a heterologous expression system. It had an intermediate molecular weight which is beneficial for serum stability, biodistribution and solid tissue penetration.

The following examples provide the teaching starting from which variants can be prepared. The examples are therefore in no way intended to be limiting the invention. In the examples "VH", "CH1", "CL" and "VL" are used for domains derived from the first antibody. "VH2" and "VL2" are used for domains derived from the second antibody. "VH3" and "VL3" are used for domains derived from the third antibody.

BRIEF DESCRIPTION OF THE FIGURES

In the examples reference is made to the following figures.

EXAMPLES

Materials and Methods
Preparation of Constructs
Bacterial Strains and Cell Lines

*E. coli* MC1061 (F$^-$araD139 Δ(ara-leu)7696 galE15 galK16 Δ(lac)X74 rpsL (Str$^r$) hsdR2(r$_k^-$m$_k^+$) mcrA mcrB1) and DH5α (endA1 hsdR17 (r$_k^-$m$_k^+$) supE44 thi-1 recal gyrA (Nal$^r$) relA1 Δ(lacIZYA-argF)U169 deoR (Φ80dlacΔ(lacZ)M15)) were used for transformations and DNA isolations.

The bacteria were grown in LB medium, supplemented with 100 μg/ml triacillin. The COS-1 cell line, derived from monkey CV-1 kidney cells, was used for eukaryotic expression. HEK293T, a human embryonic kidney cell line transfected with SV40 large T-antigen (SV40T tsA1609) (DuBridge et al., 1987) was used for eukaryotic expression. TE$_2$ cells are murine, CD3 positive "T helper"-1 cells (Grooten et al., 1989), and were cultured in RPMI1640 medium (GibcoBRL life technologies, Paisly, UK) supplemented with 30 U/ml recombinant murine IL2, 0.06 mM βME, 10% FCS, 0.03% L-glutamine, 100 U/ml penicillin, 100 mg/l streptomycin and 0.4 mM sodium pyruvate. Mouse fibrosarcoma derived MO$_4$ cells were cultured in REGA-3 medium (GibcoBRL) supplemented with 10% FCS, 0.03% L-glutamine, 100 U/ml penicillin, 100 mg/l streptomycin and 0.4 mM sodium pyruvate. MO$_4$I$_4$ (hPLAP$^+$) cells are MO$_4$ cells transfected with the hPLAP gene (Smans et al., 1995; Hendrix et al., 1991). BCL1$^{vitro}$ cells (gift from Dr. Thielemans) were cultured as TE$_2$ cells but with IL2.

Plasmids and Gene Assembly

Restriction enzymes were purchased from GibcoBRL life technologies (Paisly, UK), Vent DNA polymerase was from New England Biolabs (Beverly, Mass., USA), T4 DNA ligase, Klenow enzyme and T4 DNA polymerase were from Boehringer Mannheim (Mannheim, Germany). All enzymes were used as recommended by the manufacturers.

All primers for PCR amplification were purchased from GibcoBRL. DNA amplification was performed in a Biometra heat block using a predenaturing step of 10 min at 94° C., followed by 30 cycles, containing a denaturing step (94° C.), an annealing step (55° C.), and an extension step (72° C.), each for 30 sec.

Figure 1:
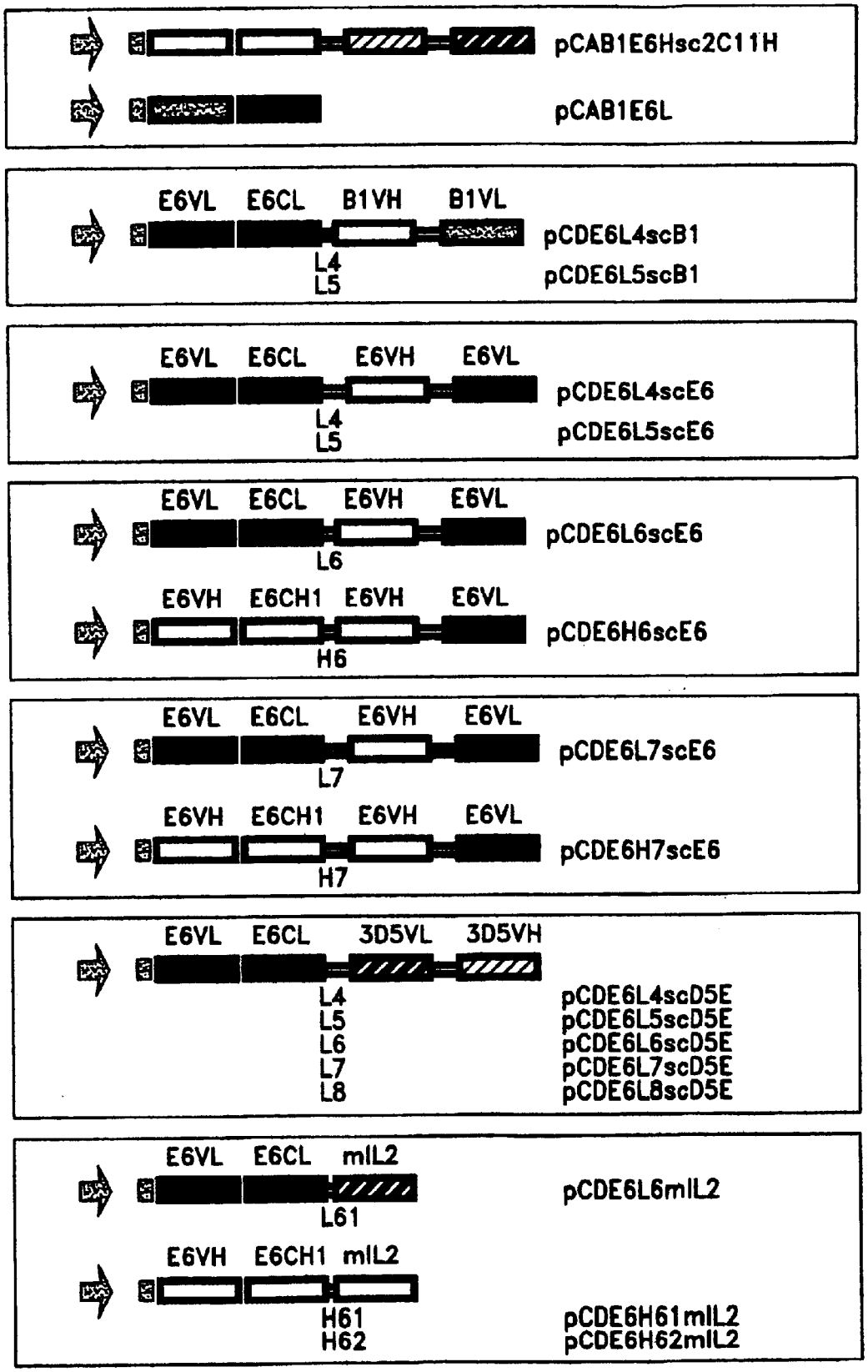
FIG. 1: Diagram of the pSV51 (Huylebroeck et al., 1988), pCAGGS (Niwa et al., 1991) and pCDNA3.1zeo$^-$ (Invitrogen, Carlsbad, Calif., USA) expression vector inserts used for transfection. E6=parental anti hPLAP antibody, 2C11=derived from the 145-2C11 parental anti CD3 antibody, B1=parental anti BCL1 antibody, 3D5=parental anti (His)$_{5-6}$ antibody, VL and CL=variable domain and constant domain of the light chain, VH and CH1=variable and first constant domain of the heavy chain, B1a= *Escherichia coil* β-lactamase, mIL2=murine interleukin 2. All light chain domains of E6 are in black, all heavy chain domains of E6 in white. 2C11scFv and 3D5scFv domains are hatched. B1scFv domains, B1a and mIL2 are in grey.

All expression modules are schematically represented in FIG. 1.

The cloning of the light chain (L) and the truncated heavy chain fragment (Fd) of the parental murine anti hPLAP mAB E6 (IgG2b, κ) in the vectors pSV51E6L (LMBP2142) and pSV51E6Hf1 (LMBP2143), respectively, was described previously (De Sutter et al., 1992a).

pSVE6sFvE6CL

A single-chain fragment of the anti hPLAP VH and VL was cloned in the vector pSV51E6sFv (LMBP3609, unpublished and provided by S. Dincq and K. De Sutter, VIB-RUG, Gent) and was used to replace VL in pSV51E6L (De Sutter et al., 1992a) by BanII-AvaI fragment exchange. The resulting vector pSVE6sFvE6CL encodes E6scFv-CL.

pSV2C11sFvE6CH1E

The vector pc/DNA/AMP containing the anti CD3 scFv in the VL-L-VH configuration was kindly provided by Dr. D. Segal (Bethesda, Md., USA). Via site directed mutagenesis with the linker 5' CCGTCTCCTCA<u>GAGCTC</u>CAAAAACCC 3'(SEQ ID NO:1) a SacI site (underlined) was created immediately after the scFv. In the vector pSV51-2C11sFvMG2fEtag, the BamHI-SacI flanked 2C11scFv was fused in front of the E-tagged mouse IgG2b Fc-portion. In this vector we replaced the mouse heavy chain fragment with PCR amplified CH1 domain, digested with SacI and NotI. The CH1, domain was amplified from the vector pSV51E6Hf1 with the forward primer 5' CACTGCC<u>GAGCTC</u>CCAAAAC 3' (SEQ ID NO.2) (SacI site underlined) and the reversed primer 5' TCATGTC<u>GCGGCCGC</u>GCTCTA 3' (SEQ ID NO:3) (NotI site underlined). As a result the vector pSV2C11sFvE6CH1 was coding for 2C11scFv-CH1. Finally, the CH1 domain was exchanged with the E-tagged CH1 domain from the vector pCAsc2C11E6Hf (see below) by a BalI-SalI restriction digest. This resulted in the vector pSV2C11sFvE6CH1E.

pSVB1aE6CH1E

The pSV71 vector containing the B1aL1Hi insert (De Sutter et al., 1992b) was the source of the EcoRV-SacI insert that replaced the EcoRV-SacI excised 2C11scFv from pSV2C11sFvE6CH1E. In this way pSVB1aE6CH1 E was made, coding for B1a-CH1. The 14 amino acids of linker 1 (SEQ ID NO:4) (VNHKPSNTKVDKRV=last amino acids of mouse IgG2b CH1 and part upper hinge) and the amino acids of the SacI site (EL) are linking both subunits, adding up to a 16 amino acid linker connecting CH1 and B1a.

pCAGGSE6L

The eukaryotic expression vector pCAGGS was a gift from Dr. J. Miyazaki (University of Tokyo, Japan) (Niwa et al., 1991) and contains an ampicillin resistance gene, the strong constitutive β-actin/β-globin hybrid promoter and part of exon 3, 3' UTR and polyA signal of the rabbit β-globin gene. pCAGGSE6L (LMBP3547-IDA97-33, unpublished and kindly provided by Dr. J. Demolder, VIB-RUG, Gent) was made by ligating the XbaI fragment (filled-in with Klenow DNA polymerase) from pSV51E6L containing the E6L-sequence to a MscI-opened vector fragment of pCAGGS.

pCA2C11sFvE6Hf

2C11scFv-Fd gene assembly was achieved in the vector pCA2C11sFvE6Hf (LMBP3715-IDA97-34) containing the following fragments (clockwise): MscI-opened vector pCAGGS (Niwa et al., 1991); SspI-BamHI fragment from pSV51 (Huylebroeck et al,. 1988), 2C11scFv encoding fragment from pcDNA/AMP/2C11 (Jost et al., 1994) cut in the BamHI- and in a introduced Ecl136II-site; Fd encoding fragment from pSV23SE6Hm (Dr. W. Lammerant, RUG, Ph.D. thesis 1994) flanked by KpnI(T4 blunted) and the 2 nucleotides of the BanII-site; NotI(Klenow blunted)-BsmI (T4-blunted) fragment from pCANTAB5E (Pharmacia LBK Biotechnology, Uppsala, Sweden) encoding the E-tag; SalI (blunted)-XbaI(blunted) fragment of pSV51.

pSVE6H1sc2C11M

The Fd-H1-2C11scFv fusion gene in pSVE6H1sc2C11M was made by ligating the NdeI(Klenow blunted)-AvaI fragment of pcDNA/AMP/2C11 (Jost et al., 1994) in the ApaI (T4 blunted)-SalI vector fragment of pSV51E6H (De Sutter et al., 1992a), encoding the E6 heavy chain that was truncated after the third amino acid of the hinge region (Fd, no cysteins included). The connecting sequence (encoding the additional EPSG) between E6Fd and 2C11 scFv was confirmed by DNA sequence analysis. This anti CD3 scFv was in the VL-linker-VH configuration and carried an c-myc tag.

pCAE6H1sc2C11H

The Fd-H1-2C11scFv fusion gene in pCAE6H1sc2C11H was also made by ligating a PCR-amplified 2C11scFv-encoding fragment to the C-terminus of E6Fd. The PCR fragment encodes the the 2C11scFv in the VH-VL configuration with a $(His)_6$ tail and it was amplified from pQE-bssFvB1-2C11 (De Jonge et al., 1995, kindly provided by Dr. K. Thielemans, VUB, Belgium) with the forward primer 5' GGCCCATGGAGGTCAAGCTGGTGGAGTC 3' and the reverse primer 5' ATA GGATCCTTATCCGGACCTTTTATTTCCAGCTTGGT GCCAG 3' (BamHI site underlined). This PCR fragment was cut in the BamHI site and kinated. Subsequently we cloned in the MscI-BglII opened pCAGGS vector (Niwa et al., 1991), the HindIII(blunted)-ApaI fragment of pSV23sE6Hm (Dr. W. Lammerant, RUG, Ph.D. thesis 1994), encoding the Fd fragment, and the PCR fragment, encoding 2C11scFv.

pCAE6H2sc2C11H

Fd-H2-2C11scFv gene assembly was achieved in the vector pCAE6H2sc2C11H (LMBP3716-IDA97-35), containing the following fragments: MscI-BstXI opened pCAGGS vector (Niwa et al., 1991); HindIII(blunted)-ApaI fragment of pSV23sE6Hm (Dr. W. Lamerant, RUG, Ph.D. thesis 1994) encoding the Fd fragment; PCR fragment amplified from pQE-bssFvB1-2C11 (De Jonge et al., 1995) with the forward primer 5' GCTGAAA GGGCCCGGTGGAGG 3' (ApaI site, underlined) and with the reverse primer 5' GGTC CCAGGGCACTGGCCTCACTCTAGAG 3' (BstXI site, underlined). This PCR fragment encodes a $(G_4S)_3$.linker, a anti murine CD3ε scfv in the VH-VL configuration and a $(His)_6$-tail.

pCAE6L2sc2C11

The E6L-L2-2C11scFv gene assembly was performed in the vector pCAE6L2sc2C11, containing the following fragments: HpaI-BstXI opened pCAGGSE6L vector; PCR fragment (coding for CL) amplified from pCAGGSE6L with the forward primer: 5' CAGTGAGCAGTTAACATCTGG 3' (SEQ ID NO:9) (HpaI site, underlined) and with the reversed primer: 5' CCTTTGGGGCCCACACTCATTCC 3' (SEQ ID :10) (ApaI site, underlined); PCR fragment amplified from pQE-bssFvB1-2C11 (De Jonge et al., 1995) with the forward primer: 5' GCTGAAAGGGCCCGGTGGAGG 3' (SEQ ID NO:11) (ApaI site, underlined) and with the reversed primer: 5' GTG CCAGGGCACTGGTTAAGATCTGGATCC 3' (SEQ ID NO:12) (BstXI site, underlined). This PCR fragment encodes a $(G_4S)_3$-linker, a anti murine CD3ε scFv in the VH-linker-VL configuration and a stop codon.

pCAB1E6H2sc 2C11H

The chimeric Fd chain with variable sequences derived from the anti BCL1 mAb B1 and the constant sequence derived from the anti hPLAP mAb E6: VH(B1)-CH1 (E6) coupled to the anti murine CD3 2C11scFv was assembled in the pCAB1E6H2sc2C11H vector as follows: the B1VH domain, together with its natural signal sequence, was PCR amplified from the vector pEFBOS-bssFvB1-2C11 (kindly provided by Dr. K. Thielemans, VUB, Belgium with the forward primer 5' CCTCACCTCGAGTGATCAGCACTG 3' (SEQ ID NO:13) (XhoI site underlined) and the reverse primer 5' CCACCTGAGGAGACAGTGACC 3' (SEQ ID NO:14) (Bsu36I site underlined). Subsequently the E6CH1 in pCAE6H2sc2C11H was flanked with a Bsu36I site by PCR amplification using the forward primer 5' CTGCCT CCTCAGGCAAAACAACACCC 3' (SEQ ID NO:15) (Bsu36I site underlined), the reverse primer 5' GGAC-CCAGTGCATGCCATAGCC 3' (SEQ ID NO:16) (SphI site underlined). These two PCR fragment were ligated in the XhoI-SphI opend vector pCAE6H2sc2C11H.

pCAB1E6L

The VL(B1)-CL(E6) chimeric light chain was assembled by substituting the DNA sequence of the mature VL(E6) gene in pCAGGSE6L with that of the mature VL(B1). The resulting vector pCAB1E6L contains the following fragments (clockwise): XbaI-Tsp45I fragment of pCAGGSE6L encoding the E6H signal sequence; the VL(B1) sequence amplified from pgFBOS-bssFvB1-2C11 wit the forward primer 5' GGATGTGACATTGTGATGACC 3' (SEQ ID NO:17) (Tsp45I site underlined) and the reverse primer 5' GATCCTTTGAGCTCCAGC 3' (SEQ ID NO:18) (SacI site underlined), the CL(E6) sequence amplifed from pCAGGSE6L With the forward primer 5' GTTG GAGCTCAAACGGGCTG 3' (SEQ ID NO:19) (SacI site underlined) and the reverse primer 5' GGA GCTGGTGGTGGCGTCTCAGGACC 3' (SEQ ID NO:20) (BsmBI site underlined); XbaI-BsmbI opened vector pCAGGSE6L.

pCDE6L4scB1 and pCDE6L4E6

The construction strategy of this plasmid involves the construction of pCAGGSE6Lm2. This construct was made by PCR amplification of the E6L gene from pCAGGSE6L (Dr. J. Demolder, VIB-RUG) with the forward primer 5' ATACCG CTCGAGACACAGACATGAGTGTGCCCACTC 3' (SEQ ID NO:21) (XhoI site underlined) and the reverse primer 5' CGC GGATCCTTACCCGGGGACGTCACACTCATTCCTG TTGAAGCTCTTGAC 3' (SEQ ID NO:22) (BamHI site underlined) with the purpose to create additional cloning sites at the N- and C-terminus of the E6L gene.

For the construction of pCDE6L4scB1, the B1scFv was PCR amplified from the vector pFE12-B1(kindly provided by Dr. K. Thielemans) with the forward primer 5' TCC CCCGGGGAAGTGAAGCTGGTGGAGTCTG 3' (SEQ ID NO:23) (SmaI site underlined) and the reverse primer: 5' ATA GGATCCTTATCCGGATTTCAGCTCCAGCTTGGTCC CAGC 3' (SEQ ID NO:24) (BamHI site underlined). This PCR fragment was digested with BamHI and phosphorylated. Subsequently the PCR fragment was ligated with the SmaI-BsaI vector fragment of pCAGGS and the BsaI-BamHI fragment of pCDNA3.1zeo⁻ (Invitrogen). In this way a hybrid vector frame was created, designated as pCD, who's promotor region is derived from the pCAGGS vector and who's 3' untranslated region, zeocin resistance gene and multi-cloning site are derived from the vector pCDNA3.1zeo⁻.

pCDE6L4scE6 was constructed in exactly the same way, only the E6scFv gene was amplificated from pSV51E6sFv (S. Dincq, VIB-RUG) with the forward primer: 5' TCC CCCGGGCAGGTTCAGCTGCAGCAGTCTGGAG 3' (SEQ ID NO:25) and the reverse primer 5' ATA GGATCCTTATCCGGACCGTTTTATTTCCAGCTTGGTCC 3' (SEQ ID NO:27)

pCDE6L5scB1 and pCDE6L5scE6

These two constructs are immediately derived from the pCDE6L4scB1 and pCDE6L4scE6 vectors by inserting two complementary adaptor oligonucleotides in the AatI and XmaI sites between the E6L and the scFv genes. The oligonucleotides 5' CGACGGTGGTTCTAGAGGTGAT-GWC 3' and 5' CCGGGCCCATCACCTCTAGAACCAC-CGTCGACGT 3' (SEQ ID NO:28) were allowed to hybridize, resulting in AatI and XmaI sticky ends and the adaptor was then cloned.

pDCDE6L6scE6

This vector contains the following fragments (clockwise): XhoI-Bsp120I(blunted) fragment of pCAE6L2sc2C11 encoding E6L, AatII(blunt)-XHoI vector fragment of pCDE6L4scE6 encoding E6scFv.

pCDE6L6scE6

This vector contains the following fragments (clockwise): XhoI-Bsp120I(blunted) fragment of pCAE6L2sc2C11 encoding E6L, AatII(blunt)-XhoI fragment of pCDE6L4scE6 encoding E6scFv.

pCDE6L7scE6

This vector contains the following fragments (clockwise): XhoI-Bsp120I(blunted) fragment of pCAE6L2sc2C11encoding E6L, two complementary oligonucleotides: 5' GGCCTCAACCACAACCTCAGCCG-CAACCTCAACCTGGGC 3' (SEQ ID NO:29) and 5' CCGGGCCCAGGTTGAGGTTGCGGCTGAG-GTTGTGGTTGA 3' (SEQ ID NO:30) that form Bsp120I and XmaI sticky ends, XmaI-XhoI vector fragment of pCAE6L6scE6.

pCDCDE6H7scE6

This vector contains the following fragments (clockwise): XhoI-Bsp120I fragment of pCDE6H6scE6 encoding E6Fd, two complementary oligonucleotide 5' GGCCTCAACCA-CAACCTCAGCCGCAACCTCAACCTGGGC 3' (SEQ ID NO:31), and 5' CCGGGCCCAGGTTGAGGTTGCGGCT-GAGGTTGTGGTTGA 3' (SEQ ID NO:32) that form Bsp120I and XmaI sticky ends, XmaI-XhoI vector fragment of pCDE6L6scE6.

Constructs with 3D5scFv

The plasmid pAK100His2 (Knappick et al., 1994), coding for the anti His scFv 3D5, was a kind gift of Dr. A. Plückthun (Zurich, Switzerland). The 3D5 scFv was amplified from pAK100His2 with the forward primer 5' TCC CCCGGGGACATTTTGATGACCCAAACTCCAC 3' (SEQ ID NO:33) (SmaI site underlined) and the reverse primer 5' ATAGGATCCTTA TCCGGATTCGGCCCCCGAGGCCGCAGAGACAG 3' (SEQ ID NO:34) (BspDEI site underlined) and was fused to an E-tag coding sequence ( TCCGGAGCGCCGGTGCCGTATCCAGATCCGCTGG AACCACGTGGCGCCTAAGGATCC, (SEQ ID NO:35) BspEI site underlined) in the pCD vector. The SmaI-SpeI fragment of this construct, encoding the E-tagged scFv 3D5 (abbreviated 3D5E), was used to assemble the following vectors:

pCDE6L4sc3D5E: Fragment 3D5E ligated to SpeI-SmaI fragment of pCDE6L4scB1
pCDE6L5sc3D5E: Fragment 3D5E ligated to SpeI-SmaI fragment of pCDE6L5ScB1
pCDE6L6sc3D5E: Fragment 3D5E ligated to SpeI-SmaI fragment of pCDE6L6scE6
pCDE6L7sc3D5E: Fragment 3D5E ligated to SpeI-SmaI fragment of pCDE6L7SCE6
pCAE6L8sc3D5E: Fragment 3D5E ligated to SpeI-SmaI fragment of pCAE6LM2 pDCDE6L61mIL2

The E6L-mIL2 fusiongene was assembled by ligating the following fragments: XhoI-Bsp120I(blunt) fragment of pCDE6L6scE6 encoding E6L, NdeI(blunt)-BamHI fragment of pLT10mIL2ST (Mertens et al., 1995) encoding mIL2, and the XhoI-BamHI vector fragment of pCDE6L4sc3D5E.

pCDE6H61mIL2 and pCDE6H62mIL2

These vectors were assembled by ligating the following fragments: the XhoI-BamHI vector fragment of pCDE6L4sc3D5E, NdeI(blunt)-BamHI fragment of pLT10mIL2ST encoding mIL2 and a fragment of pCDE6H6scE6 encoding E6Fd, excised with XhoI-Bsp120I (blunt) for the H61 linker or cut with XhoI-XmaI for the H62 linker.

Plasmids for Electroporation of SP2/0 cells

In the vector pCAB1E6L a zeocin resistance gene was inserted by replacing the BglII-ScaI fragment of the pCAGGS vector with the BamHI-ScaI fragment of the pCDNA3.1zeo⁻vector (Invitrogen, Carlsbad, Calif., USA). This new plasmid was named pCDB1E6Lzeo. Analogously a neomycine resistance gene was inserted in pCAB1E6H2sc2C11H by replacing the HindIII-ScaI fragment of the vector, with the HindIII-ScaI fragment of pCDNA3 (Invitrogen). This resulted in the vector pCDB1E6H2sc2C11Hneo.

Transfection Protocols

Unless otherwise stated, all cultures were grown at 37° C. with 5% $CO_2$ in Dulbecco minimal essential medium (DMEM, GibcoDRL life technologies, Paisly, UK) supplemented with 10% FCS, 0.03% L-glutamine, 100 U/ml penicillin, 100 mg/l streptomycin and 0.4 mM sodium pyruvate.

Transfection of COS-1 cells was performed as described in De Sutter et al. (1992). HEK293T (DuBridge et al., 1987) cells were transfected by a $Ca_3(PO_4)_2$ method. 20 h before transfection, subconfluent monolayers were trypsinized and reseeded at $2.25 \times 10^6$ cells/75 $cm^2$. 2 h before transfection 35 ml of fresh medium was added to the cells. 14 µg of sterile, ethanol precipitated DNA of each expression plasmid (purified on a Qiagen DNA purification column, Qiagen Inc., Calif., USA) was redissolved in 1400 µl 0.1×TE buffer (1×TE: 10 mM Tris.HCl, 1 mM EDTA) pH 7.5, and mixed with 350 µl 1.25 mM $CaCl_2$, 125 mM Hepes-NaOH, pH 7.5. This DNA-solution was slowly added to 1×Hepes/2×BS (25 mM Hepes-NaOH pH 7.5; 16 g/l NaCl; 0.74 g/l KCl; 0.50 g/l $Na_2HPO_4$. 12 $H_2O$; 2 g/l Dextrose) while continuously shaking. After 1 minute additional shaking, the mixture was transferred to the medium covering the cells and incubated for 24 h at 37° C.

Subsequently, the mixture was removed from the cells and replaced by 35 ml DMEM supplemented with 0.03% L-glutamine, 100 U/ml penicillin, 100 mg/l streptomycin, 0.4 mM sodium pyruvate, 5 mg/l bovine insulin, 5 mg/l transferrin and 5 µg/l selenium. Medium was harvested after 24 or 72 h. Dead cells were removed from the medium by centrifugation at 1100 rpm for 5 min and the culture supernatant was concentrated over a membrane with a cutoff value of 10 kDa (Centricon-10® microconcentrator or a Centriprep-10® concentrator membrane, Amicon Inc., Beverly, Mass., USA).

In order to change the buffer, the concentrated supernatant containing the bispecific antibody (35 ml to 2.5 ml on Centriprep-10) was diluted with 12.5 ml PBS(A) (=171.1 mM NaCl, 3.4 mM KCl, 10 mM $Na_2HPO_4$, $12H_2O$, 1.8 mm $KH_2PO_4$) supplemented with 0.05% bovine serum albumin (BSA) and 0.02% azide, and concentrated again to 1.5 ml. Cells were lysed with 10% NP-40 (Nonidet P40), containing 10% aprotenin, 100 mM Tris.HCl, pH 8.0, and 10 mM EDTA.

HEK293T Production of Fab-scFv BsAb

For HEK293T production of 1 mg bispecific B1Fab-scFv we seeded $4 \times 10^7$ HEK293T cells in 10 cultureflasks of 175 $cm^2$ and after 24 hours these cells were cotransfected with pCAB1E6L and pCAB1E6H2sc2C11H (140 µg of each plasmid) using the standard $Ca_3(PO_4)_2$ transfection method described. After 24 h the precipitate was removed and the cells were allowed to grow in ITS supplemented medium. Every 48h, this medium was harvested and changed. This was repeated six times resulting in 1.75 l medium that was filtered with a bottle top filter (Nalgene).

Electroporation of Fab-scFv in OP2/0 Cells

SP2/0-Agl4 cells, growing in log phase were harvested and resuspended at $4 \times 10^6$ cells in 400 µl growing medium (RPMI 1640, supplemented with 10% foetal calf serum, 0.03% L-glutamine, 100 U/ml penicillin, 100 mg/1streptomycin, $5 \times 10^{-5}$ βME and 0.4 nM sodium pyruvate) and kept on ice. 15 µg of each plasmid (pCDB1E6Lzeo and pCDB1E6H2sc2Ca11Hneo) was linearized by a ScaI digest. The plasmids were ligated and the mixture was purified by a phenol-ether extraction, precipitated and resuspended in 20 µl bidest. 1 minute before electroporation the DNA was mixed with $4 \times 10^6$ cells in the electroporation cuvet (gap 0.4 cm) and kept on ice. The electric pulse (900 µF, 250 V) was generated by an ASYJECT Plus (Molecular Technologies inc., St Louis, Mo., USA). Immediately after the pulse 1 ml of fresh medium was added to the cells and they were transferred to a 12 $cm^3$ culture plate. 48 h later the electroporated cells were incubated with growing medium containing 0.6 mg/ml zeocin) and 0.6 mg/ml neomycin. After 30 days the surviving cells were transferred to larger culture flasks or diluted for subcloning, and the culture medium was analysed.

Characterization of Expressed Proteins

Concentrated medium fractions of transfected cells corresponding to 500 µl supernatant, were diluted with 3× non-reducing sample buffer (New England Biolabs, Beverly, Mass., USA), boiled for 5 min and subjected to 10% SDS-PAGE (Laemmli, 1970). After gel electrophoresis, the proteins were transferred to a nitrocellulose membrane (BASS; 0.45 µm; Schleicher & Schuell, Dassel, Germany) using the semi-dry Multiphor II NovaBlot system (1 $mA/cm^2$; 1.5 h; Pharmacia LBK Biotechnology, Uppsala, Sweden).

Subsequent detection of the proteins on the blot was performed as follows: after blocking the membrane in blocking solution (5% (w/v) reconstituted, dried skimmed milk in 50 mM Tris.HCl, pH 8.0, 80 mM NaCl, 3 mM $NaN_3$ and 0.2% NP-40), the blots were incubated for 1.5 h with the anti murine γ and κ detection sera each 1:1000 diluted in blocking solution (goat anti murine Ig serum and goat anti murine κ serum, both 1 mg/ml, Sera-Lab LTD, Crawley Down, U.K.). Subsequently the blots were washed three times with blocking solution and incubated for another 1.5 h with rabbit anti goat IgG serum conjugated to alkaline phosphatase (Sigma Immuno Chemicals, St-Louis, Mo., USA) 1:7500 diluted in blocking solution. Finally, the membrane was washed extensively with substrate buffer (0.1 M Tris.HCl, pH 9.5, 0.1 M NaCl and 50 mM $MgCl_2$) and then developed by incubation with nitro-blue-tetrazolium and 5-bromo-4-chloro-3-indolyl phosphate (Promega, Leiden, The Netherlands) in substrate buffer. This staining reaction was stopped by rinsing the blot with water.

The antigen-binding capacity after blotting was analyzed by incubation of the blocked filter with soluble hPLAP (Sigma Chemical Co., St-Louis, Mo., USA, final concentration 0.1 U/ml in blocking solution), followed by the specific enzymatic staining reaction as described above.

For densitometric measurements, the blots containing immunoreactive signals were scanned with a desktop scanner and analyzed by the whole Band Analyses software (Bio Image, Ann Arbor, Mich., USA). The integrated intensity was calculated for each lane in terms of percentage.

Anti E-tag immunodetection was achieved with an murine anti E-tag antibody (1:1000, Pharmacia LBK Biotechnology, Uppsala, Sweden). Anti His-tag immunodetection was achieved with anti-His tag antibody (Qiagen Inc, Valencia, Calif., USA ).

Both incubation steps were followed by a anti-murine IgG1 serum conjugated to alkaline phosphatase (Pharmingen, San Diego, Calif., USA). Subsequent enzymatic staining was performed as described above.

The purified and biotinylated BCL1 IgM molecule was a kind gift of Dr. K; Thielemans (VUB, Belgium). It was used in a final concentration of 1 µg/ml to incubate immunoblots containing the B1Fab-scFv or B1scFv molecule. Subsequently the blot was treated with streptavidin conjugated to alkaline phosphatase (Life Technologies, Paisley, UK) and stained with the same enzymatic reaction as described above.

IMAC Purification of Bispecific Fab-scFv

Column Preparation:

For large scale purification a Hi-Trap chelator column (Pharmacia) was used. The agarose beads of the column were thoroughly rinsed with bidest, loaded with 1 column volume of 0.1 M $NiSO_4$ and immediately rinsed with 5 column volumes of bidest.

Sample Preparation:

The HEK293T supernatant was concentrated, dialyzed to 150 ml PBS(A), supplemented with imidazole to a final concentration of 10 mM and subsequently adjusted to pH 7.5.

Purification:

The column was equilibrated with 10 volumes of starting buffer (PBS(A) containing 50 mM immidazole, 10% glycerol, pH 8.5) and loaded with the sample using a luer lock syringe. The flow trough was collected. Ten volumes of starting buffer were used to wash the column and the bispecific Fab-sFb was eluted with PBS(A) containing 400 mM immidazole, pH 8.5.

Concentration, Dialysis and Functional Analysis of the Purified B1Fab-scFv

The eluted fractions were concentrated by ultrafugation (Centricon system, Amicon), diluted in PBS(A) and concentrated again to a final volume of 300 µl. Protein concentration was measured with a Biorad DC protein assay (Bio-Rad Laboratories, Hercules, Calif., USA) and was determined to be 4 mg/ml. The final amount of purified B1Fab-scFv was 1.3 mg. The purified B1Fab-scFv was used in a T-cell proliferation assay as further described and found to be functional. 1 µg of purified BsAb gave rise to a proliferative respons comparable as with 1 µg non-purified protein (data not shown).

Flow Cytometry

TE2, CD3$^+$ Th-1 cells (Grooten et al., 1989), mouse fibrosarcoma MO4 cells, MO4I4 cells, transfected with the hPLAP gene (Hendrix et al., 1991; kindly provided by Dr. M. De Broe, University of Antwerp, Belgium) and BCL1$^{vitro}$ cells (obtained from Dr. K. Thielemans) were used for flow cytometric experiments.

Purified murine monoclonal anti hPLAP antibody E6 (De Waele et al., 1988; Flamez et al., 1995), was used to verify hPLAP expression on the KO4I4 cells. A purified fraction of the parental anti murine CD3ε 145-2C11 monoclonal antibody (Leo et al., 1987, kindly provided by Prof. Dr. J. Plum, RUG, Gent), was used to verify the CD3-expression on TE$_2$ cells (data not shown). For indirect immunofluorescence staining, TE$_2$ cells (CD3$^+$) were washed with RPMI1640 medium and resuspended (25×10$^4$ cells per sample) in 500 µl of the concentrated and dialysed, BsAb (αhPLAP×αCD3) (4 Ag) and subsequently incubated on ice for 60 min. Likewise, MO$_4$I$_4$ (hPLAP$^+$) cells were washed with RPMI medium and 25×10$^4$ cells were incubated with the BsAb (αhPLAP×αCD3). After three wash steps with incubation buffer (PBS(A) supplemented with 0.5% BSA and 0.02% NaN$_3$), the cells loaded with BsAb were incubated for 60 min on ice in a 1:1000 dilution of fluorescein-conjugated goat (Fab')$_2$ fragment to mouse IgG (Fab')$_2$ (Cappel, West Chester, UK). After a final wash procedure, all cells were resuspended in 300 µl incubation buffer and immediately analysed by flow cytometry, (FACSCalibur; Becton Dickinson, Sunnyvale, Calif.).

Green fluorescence intensity was measured for the living cell population, which was constantly kept at 4° C. Presentations of the resulting histograms were processed with the WinMDI-software (multiple document interface and Flow cytometry applications, version 2.1.3, TSRI.

Flow cytometric analysis of the bispecific character of BsAb (αBCL1×αCD3) was essentially performed in a similar procedure, but here different tumor cells and detection systems were used. For immunofluorescence staining of the TE2 (CD$^+$) cells pre-treated with BsAb (αBCL1×αCD3) (15 µg/ml) we used the biotinylated BCL1 IgM antibody (gift Dr. K. Thielemans) followed by FITC-conjugated streptavidin (Sera-Lab LTD, Crawley Down, U.K.). BCL1$^{vitro}$ cells (BCL1$^+$) were used to analyse the binding capacity of the chimeric Fab subunit of the bispecific antibody. The cells were loaded with BsAb (αBCL1×αCD3) and subsequently stained with the following detection antibodies: anti-His tag antibody (Qiagen Inc, Valencia, Calif., USA ), anti mouse IgG1 (Sigma), anti goat FITC conjugated (Sigma). Finally the green fluorescent cells were counted with a FACSCaliber cytometer.

Flow cytometric analysis of the trispecific (αhPLAP×αBCL1×αCD3) and the Fab-(scFv)$_2$ molecule was essentially performed as described above, but different detection antibodies were used; anti mouse IgG γ/κ (1:200 dilution) and chicken anti goat IgG (H+L) FITC (1:200 dilution, Chemicon, Tenecula, Calif., USA).

T-Cell Proliferation Assay

For the hPLAP tumor model we used MO4I4 tumor cells and splenic T-cells from syngenic C3H/HeOUico, for the BCL1 lymphoma cells we used T-cells from syngenic BALB/c mice. All mice were purchased from the Charles River group (Sulzfeld, Germany) and kept and treated according to guidelines issued from the local ethical commission for animal experiments.

MO4I4 and BCL1$^{vitro}$ tumor cells were pre-treated with 50 µg/ml mitomycin C at 37' C. in the dark for 12 h and 1.5 h respectively. After removal of the mitomycin C, 5×10$^4$ tumor cells were co-cultured with the corresponding 1×10$^4$ splenic T-cells in a round bottom well in the presence of the indicated concentration of the BsAb (αhPLAP×αCD3) (αBCL1×αCD3) or the trispecific molecule (αhPLAP×αCD3×αBCL1). After 48 h, the cells were pulsed with 0.5 µCi of tritium-thymidine ([$^3$H]TdR 1mCi/ml, Amersham). 18 h later the cells were lysed by freezing, the DNA was harvested with an automatic cell harvester and the incorporated radioactivity was measured by scintillation counting using a Top-count machine (Packard, Meriden, Colo., USA)

$^{51}$Cr Release Assay

Primary alloreactive CTL responses were generated and investigated with a standard $^{51}$Cr release assay. Briefly, 4×10$^6$ splenic syngenic responder cells (C3H/HeOUico for the hPLAP tumormodel, BALB/c for the BCL1 tumor model) were mixed with 4×10$^6$ splenic allogenic stimulator cells (C57B1/6) that were treated with 50 µg/ml mitomycin C for 60 min at 37° C. in the dark. The mixed cell population was cocultured in 2 ml cultures in complete medium (RPMI 1640, with 10% foetal calf serum, 0.03% L-glutamine, 100 U/ml penicillin, 100 mg/l streptomycin, 0.4 mM sodium pyruvate and 5×10$^{-5}$ M βME) in the presence of 30 U/ml mIL2. These cultures we re incubated at 37° C. in 5–7% CO$_2$ in humidified air for 5 days.

Tumor cells (MO4I4 or BCL1$^{vitro}$) were incubated with 150 µCi Na$^{51}$CrO$_4$, (Amersham, Ghent, Belgium) for 90 min at 37' C. and washed carefully (to minimize the spontaneous release). Effector cells from the mixed lymphocyte culture were harvested, washed and 25×10$^4$ cells were plated in triplicate in 96 well U-bottom plates (Falcon, Becton Dickinson, Mountain View, Calif., USA) containing 5×10$^3$ tumor cells and bispecific antibody (1 µg/ml). The effector/target ratio is 50/1 in a total volume of 200 µl. After 4 h incubation at 37° C., 30 µl of the culture supernatant was transferred to a luma-plate (Packard, Meriden, Colo., USA), air dried and measured with a Topcount machine. The percentage of specific lysis was calculated as 100× [(experimental release)−(spontaneous release)/(maximum release)−(spontaneous release)). Maximum release was the value obtained from target cells incubated with 2% SDS. The spontaneous release never exceeded 14% of the maximum release.

Serum Stability In Vitro
Serum Preparation and Sample Incubation:

Balb/c mice were treated with an anaesthetic (3.75 mg avertin) and their blood was taken by cardiac puncture. The blood was incubated at 37° C. for 60 min, then stored at 4° C. for 60 min and subsequently centrifuged at 14 000 rpm for 10 min. The serum was filter sterilised and the Fab-scFv sample was added to a final concentration of 4 µg/ml. This was divided in three batches (each 150 µl) and incubated at 37° C. in sterile conditions. After several periods of time (2 h, 12 h and 24 h), one of the batches was frozen until further analysis.

Analysis of the Remaining Activity of Fab-scFv BsAb After Serum Incubation

The serum stability of the novel Fab-scFv BsAb was investigated using a standard T-cell proliferation assay. We argued that the remaining functional activity in the serum-incubated samples is correlated to the serum stability of the bispecific protein. The frozen serum samples were submitted in triplicate to a T-cell proliferation assay as described earlier.

EXAMPLE 1

Figure 2A:
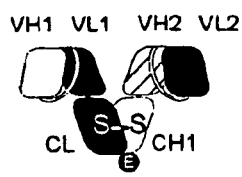
FIG. 2: Heterodimerization of CL- and CH1 containing molecules in eukaryotic cells can be dependent on the pairing of appropriate VL and VH domains.
Figure 2A:
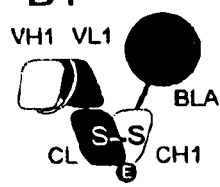
Figure 2A:
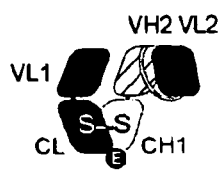
Figure 2A:
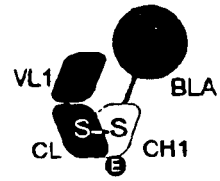
Figure 2A:
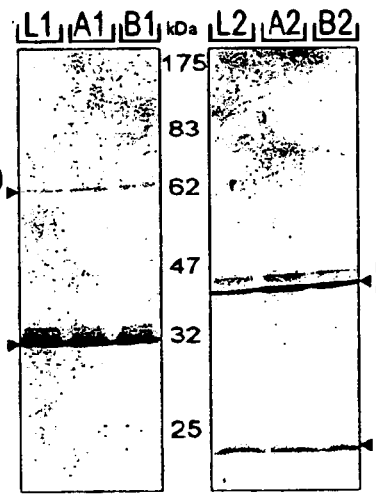

Heterodimerization by CL-CH1 Interaction in Eukaryotic Cells can Depend on Appropriate VL-VH Pairing In a first attempt, minibodies were constructed using the CL and CH1 domain on their own to promote heterodimerization of two different scFv molecules. However, after cotransfection of expression plasmids for the VH-VL-CL (scFv-CL) and the VL2-VH2-CH1 (scFV-CH2) fusion proteins, largely all secreted immunoglubulins, detected by an anti mouse IgG γ/κ serum were in the monomer format. Inclusion of an E-tag on the C-terminus of the CH1 domain, allowed for the easy discrimination between scFv-CL and the E-tagged scFv-CH1 by immunodetection with an anti E-tag antibody. This clearly showed that the monomers were not scFv-CH1 and that the slight amount of diners formed did not contain the scFv-CH1 fusion molecule, and hence consisted of scFv-CL molecules alone (data not shown). To avoid possible steric hindrance caused by the fusion of the scFv molecules to the CL and CH1 domains, a derivative was made with a longer flexible linker (16 amino acids: VNHKPSNTKVDKRVEL) (SEQ ID NO:36) seperating the fusion partner from CH1. For simplifying the analysis of the construct we used a β-lactamase molecule as a fusion partner, which allows for detection of heterodimers simply on the basis of molecular weight. When co-expressing the bla-CH1 fusion with the scFv-CL fusion, only CL-containing products could be found in the medium with anti mouse IgG γ/κ immunodetection. This is especially remarkable since this was also true when the bla-CH1 fusion was co-expressed with a native L chain. L-chains or L-chain derivatives can be expressed on their own and appear as monomers and as homodimers, so they can be secreted without association to any other partner. The bla-CH1 fusion is not expected to hinder the association of CH1-CL, so it was expected that a L:bla-CH1 dimer should be formed by the interaction of CL and CH1. No product can be seen with the expected molecular weight of the intended heterodimer (FIG. 2A). Furthermore, immunodetection with the highly sensitive anti E-tag antibody failed to reveal any trace of a L:bla-CH1 heterodimer (data not shown).

Figure 2B:
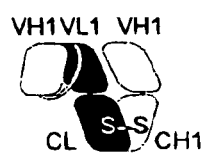
Figure 2B:
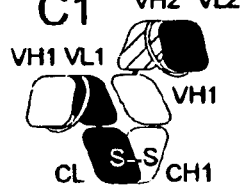
Figure 2B:
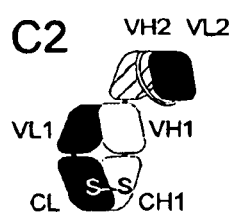
Figure 2B:
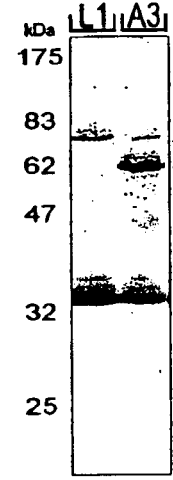
Figure 2B:
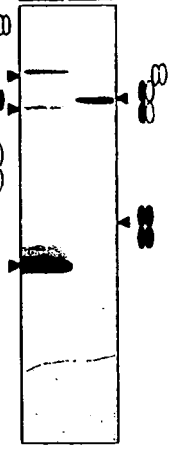

However, in the reversed situation when a scFv-CL fusion was co-expressed with a native Fd chain (VH1-CH1), a scFv-CL:scFd heterodimer could be formed (FIG. 2B, molecule A3), even when the Fd chain was N-terminally extended with another scFv (scFv-CL:scFv-Fd) (FIG. 2B, molecule C1). A more efficient heterodimerization however was observed when the scFv-Fd fusion was co-expressed with the native L chain. This resulted in a bispecific antibody by genetic fusion of a scFv fragment to the N-terminus of the Fd chain of a Fab fragment (FIG. 2B, molecule C2), which is a novel format for bispecific antibodies. Due to the fact that the hinge region is not included, both binding specificities remain monovalent.

Figure 2C:
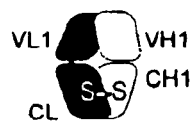
Figure 2C:
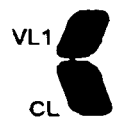
Figure 2C:
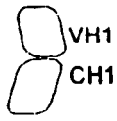
Figure 2C:
Figure 2C:
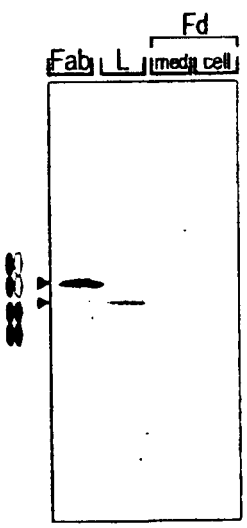

Both VL-CL:VL-CL (L:L) and VH-CH1:VH-CH1 (Fd:Fd) homodimers could theoretically be formed. Especially L-chain dimer has already been described. The Fd-chain dimer has never been observed, as is also shown in FIG. 2C: the complete Fab fragment and L-chain dimer can be expressed, while Fd expression is not detectable in the medium nor in the cellular fraction. This can possibly be due to the described association of endoplasmic chaperones such as BiP with an unpaired Fd chain. When association of the L chain is postponed, the Fd-chain could be degraded instead. BiP is an endoplasmic (retained in the ER by a KDEL-sequence) chaperone of the HSP70-family that generally binds to exposed hydrophobic patches. The association of BiP with Fd chains or to CH1 domains alone could be responsible for the failure of all scFv-CH1 or BLA-CH1 fusion molecules to pair with an L-chain or a scFv-CL fusion protein. In these molecules, the CH1 domain is not preceded by a VH domain that then could pair with an appropriate VL domain. This could be explained if BiP binds mainly to the CH1 domain, and the displacement could only occur efficiently when also the VH-VL interaction also contributes to the binding energy. If the interaction energies of CH1 with BiP or with CL are at least in the same range, displacement of the chaperone would be inefficient unless the additional free energy of binding, contributed by the interaction of VH with VL, favors displacement. Prolonged unproductive association of BiP with CH1 containing fusion molecules could then lead to targeting the molecules for degradation.

FIG. 2 shows that the heterodimerization of CL- and $CH_1$ containing molecules in eukaryotic cells can be dependent on the pairing of appropriate VL and VH domains. The expected molecules after co-expression of CL- and CH1 containing fusion proteins are schematized. Light chain derived domains are in black, heavy chain derived domains are in white, 2CL derived domains are hatched. A Western blot, developed with anti mouse IgG γ/κ serum, of a 10% non-reducing SDS-PAGE loaded with supernatant fractions from COS-1 cells, is shown. Beside the pictures of the gels the position of the molecular weight markers (kDa) is shown, as well as the configuration and position of the molecules seen on the gel.

In the figure filled symbols represent all domains from CL-containing molecules; open symbols represent domains from CH1-containing molecules.

A] Co-expression of 2c11scFv-CH1 with E6scFv-CL (molecule A1) or with the natural E6L chain (molecule A2), and of a bla-CH1 fusion (separated by an elongated linker sequence) with E6scFv-CL (molecule B1) or with the natural E6L chain (molecule B2). In lane L1 the E6scFv-CL and in lane L2 the E6L chain alone are loaded. Otherwise, the expected molecule is shown on top of each lane. In all cases, only the monomeric and dimeric light chain or light chain-derivatives are visible. This was confirmed by developing the same samples with a highly sensitive antibody against the CH1-fused E-tag.

B] Lane L1 shows expression of E6scFv-CL alone. Co-expression of E6scFv-CL with an N-terminally extended Fd chain (C1) in stead of an N-terminally extended CH1 molecule (cfr A1 and B1) did result in the formation of an expected heterodiner, although the efficiency of heterodimerization is low. The heterodimerization efficiency was increased up to more than 90% by co-expressing the scFv-Fd fusion with the natural L chain (C2).

C] Expression of the Fab chain (Fab) and of the L chain alone (L) is detectable, but expression of the Fd-chain alone cannot be detected in the medium (med), nor in the cellular fraction (cel).

EXAMPLE 2
Fab-scFv Heterodimers as a Model System for Bispecific Antibodies

One of the disadvantages of using smaller recombinant BsAb molecules such as (scFv)2 molecules or dimerized scFv molecules is the relative short reach to far apart antigens. This is especially important if the molecules are intended to link two different cells. When the Fab chains are used as a heterodimerization motif, they can constitute a binding specificity on their own. To improve upon the interaction range, the second specificity was fused to the other side (C-terminus) of the location of the binding specificity of the Fab fragment. Since a scFv molecule confers the second binding specificity, the molecular weight will still be low enough to allow rapid tissue penetration, while being high enough to avoid rapid body clearance.

The artificial peptide linker used to connect the scFv to the Fd or the L chain should not contain a functional hinge region, since this motif can be responsible for a homodimerization of two BsAbs, making them bivalent for each binding specificity. This can be a disadvantage for some applications, since some receptors can be triggered by crosslinking, leading to premature activation or inactivation of the effector cell. Monovalent binding specificities are for example of great importance when using the molecule to retarget T cells to a tumor site. A bivalent anti-CD3 binding could lead to systemic CD3 cross-linking, leading to a temporarily T cell activation and a sustained T cell anergy. Also, for some membrane markers, a bivalent binding might induce internalization and removal of the molecule from the cell surface. It is thus important to use the Fab fragment as a dimerizing unit and not the Fab'. If a functional hinge region is included, it will act as a homodimerization motif on its own, doubling the binding specificities in a substantial part of the expressed molecules, even if two different molecules are expressed together.

We have explored the possibility to create hmonovalent BsAb molecules by fusing a scFv molecule via a linker to the C-terminus of either the Fd or the L chain (FIG. 3A). Using this a as a model system for the creation of BsAb we were able to obtain very specific heterodimerization of the L with the Fd-scFv molecules. Up to more than 90% of the secreted immunoglobulin proteins was in the desired bispecific format (FIG. 3A). Furthermore, the L:Fd-scFv format allows efficient production of the BsAb from the culture medium of the transfected cells. Without amplification, up to 10 $\mu$g BsAb/ml culture medium could be obtained.

Figure 3B:
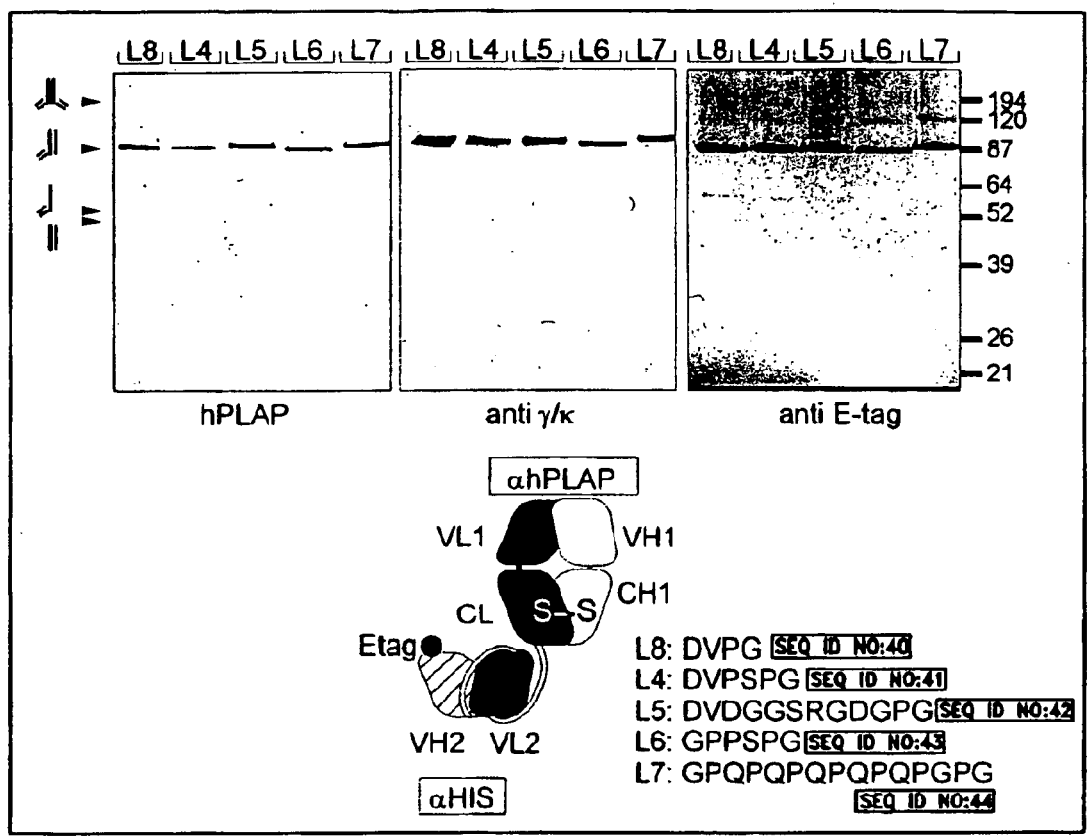
FIG. 3: Expression of C-terminal Fab-scFv fusion proteins.

Apparently, the length and composition of the peptide linker connecting the L and the scFv molecules can be varied without any significant drop in the expression of the L-scFv:Fd heterodimer (FIG. 3B). The Fab-scFv fusion protein was expressed as the major immunoglobulin derived product as is shown by immunodetection with anti IgG $\gamma/\kappa$ and anti E-tag antibodies. Revelation of the blotted proteins with hPLAP showed the functionality of the Fab fragment. A longer linker could allow a further range of reach for antigen, while a shorter linker, or a different amino acid sequence, might stabilize the fusion product. This could be important when the flexible linker should be vulnerable for proteases present in the environment where the BsAb is expected to function.

Figure 4A:
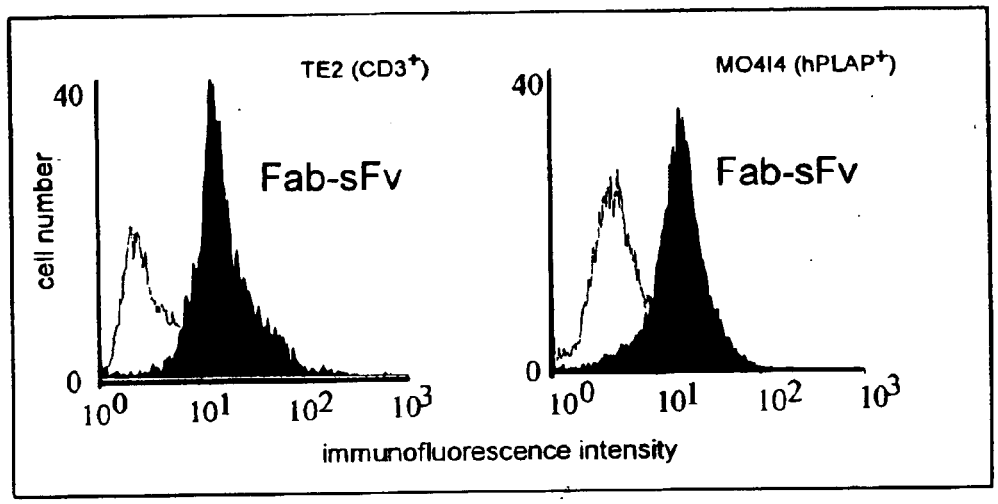
FIG. 4: C-terminal Fab-scFv fusion proteins are functional as bispecific antibodies.
Figure 4B:
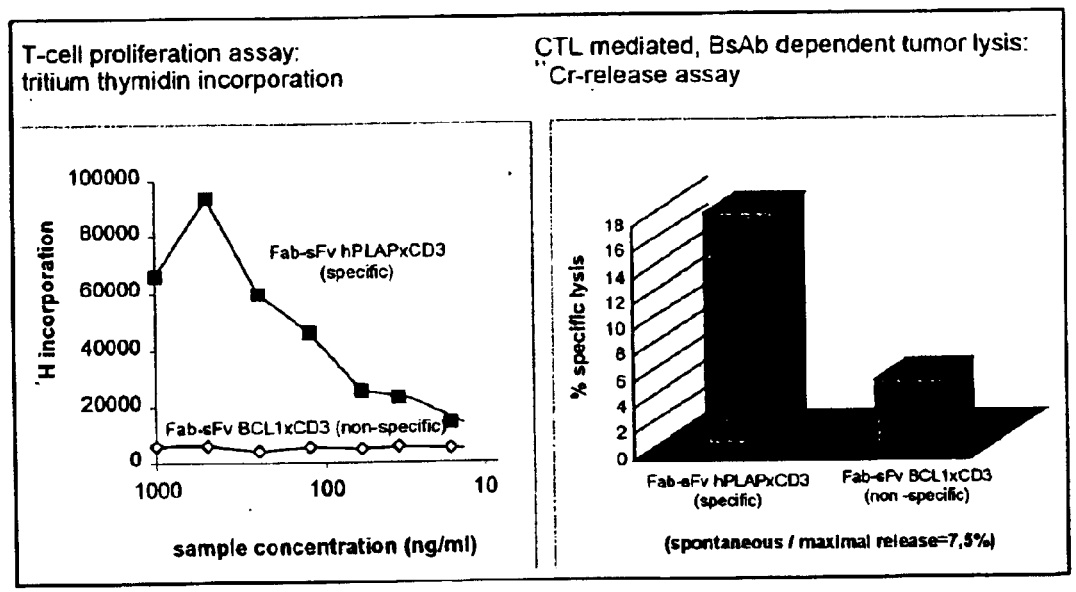

As a model for a monovalent BsAb we further characterized the ($\alpha$hPLAP)Fab-($\alpha$CD3)scFv with the (G4S)3 peptide linker (H2) for functional binding to cells expressing hPLAP ($M_4OI_4$ fibrosarcoma cells) or CD3 (TE2 T cells) on their membrane. The Fab-scFv BsAb ($\alpha$hPLAPx$\alpha$CD3) was shown to efficiently bind both cells, proving the functionality of both binding sides of this new model for BsAbs (FIG. 4A). This binding was not observed with a cells that did not express the hPLAP or the CD3 markers (data not shown). To exclude the possibility that fractions of the BsAb bind only one antigen at the same time, we assayed the functionality of the BsAb to bind two cells at the same time. This was done using a T-cell proliferation assay and a T-cell cytotoxicity assay (FIG. 4B). These assays clearly showed that indeed the BsAb could bind two different cells at the same time. A clear dose dependent T cell reaction could be seen only when the BsAb with the appropriate specificities ($\alpha$hPLAPx$\alpha$CD3), and hPLAP expressing cells were used. This clearly proves that the new Fab-scFv model is functional as a bispecific antibody derivative and can redirect CTL activity towards tumor cells.

Figure 5A:
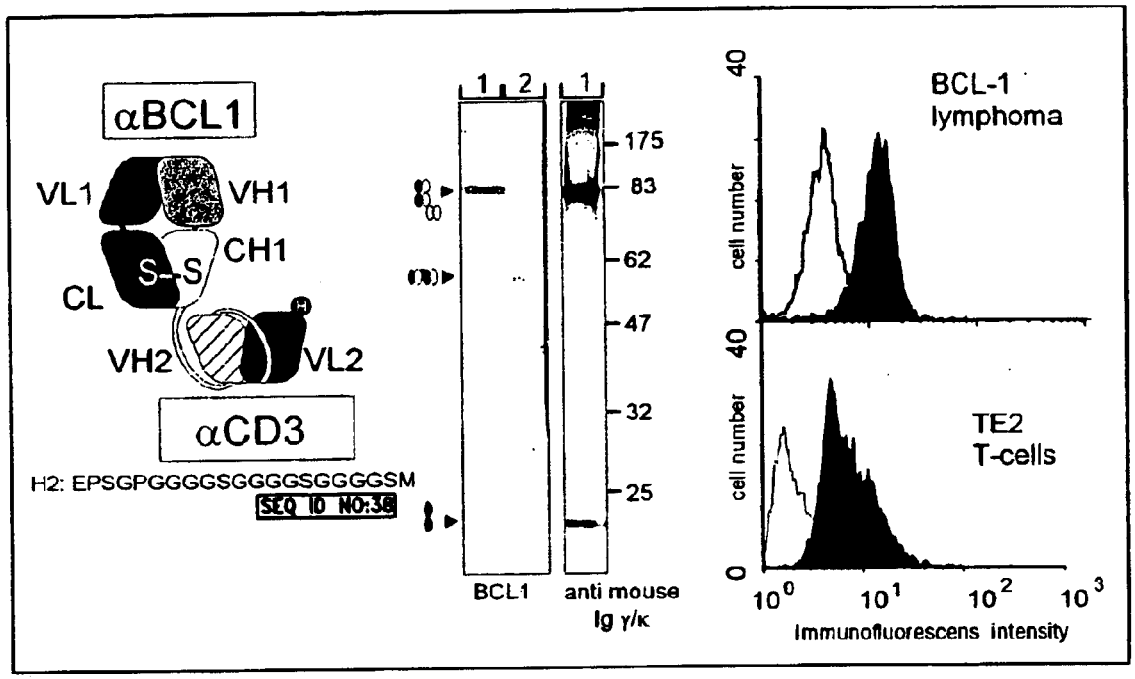
FIG. 5: Chimeric L:Fd chains molecules can be used to heterodinerize Fab-scPv bispecific antibodies.
Figure 5B:
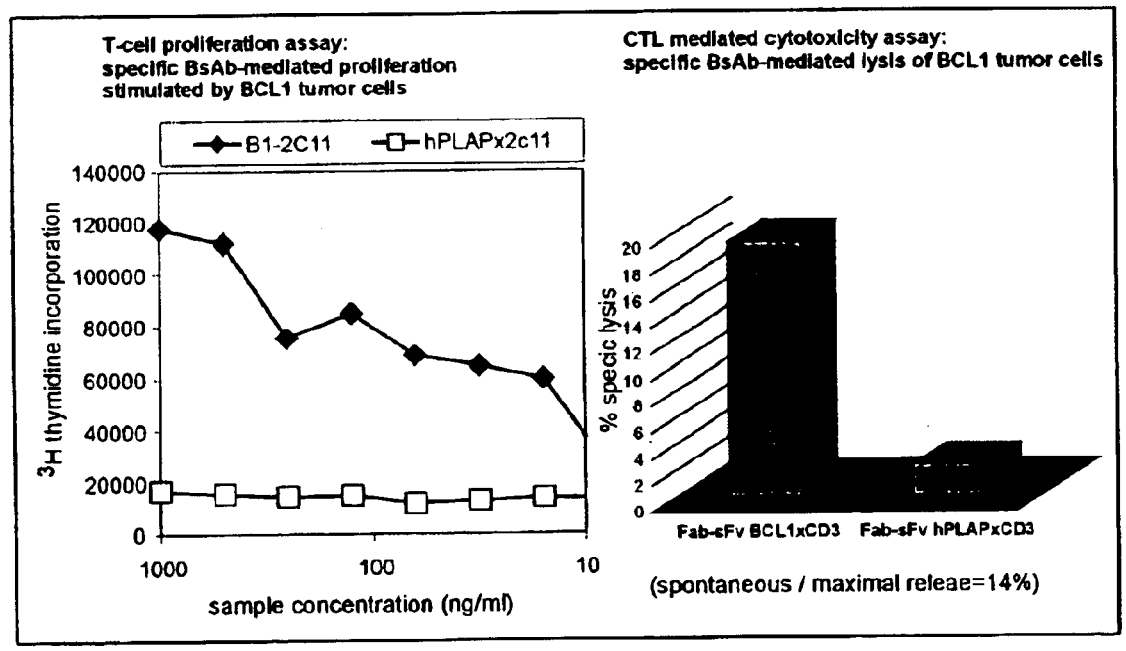

The Fab part of the molecule can also be a hybrid molecule, where the different domains are derived from different antibodies. Such a chimeric Fab can be constituted from a VH and a VL with a defined specificity, fused to constant domains derived from a different antibody. In FIG. 5A the expression of a BsAb containing a hybrid Fab fragment with VH and VL domains derived from the B1 anti-BCL1 antibody and constant domains from the E6 anti-hPLAP antibody is shown to be successfully produced. Again the heterodimerization of the desired bispecific molecule was very selective. The functionality of the binding specificities was shown by flow cytometry and by functionality in a T-cell proliferation assay and an antibody directed T-cell lysis assay (FIG. 5B).

Figure 6A:
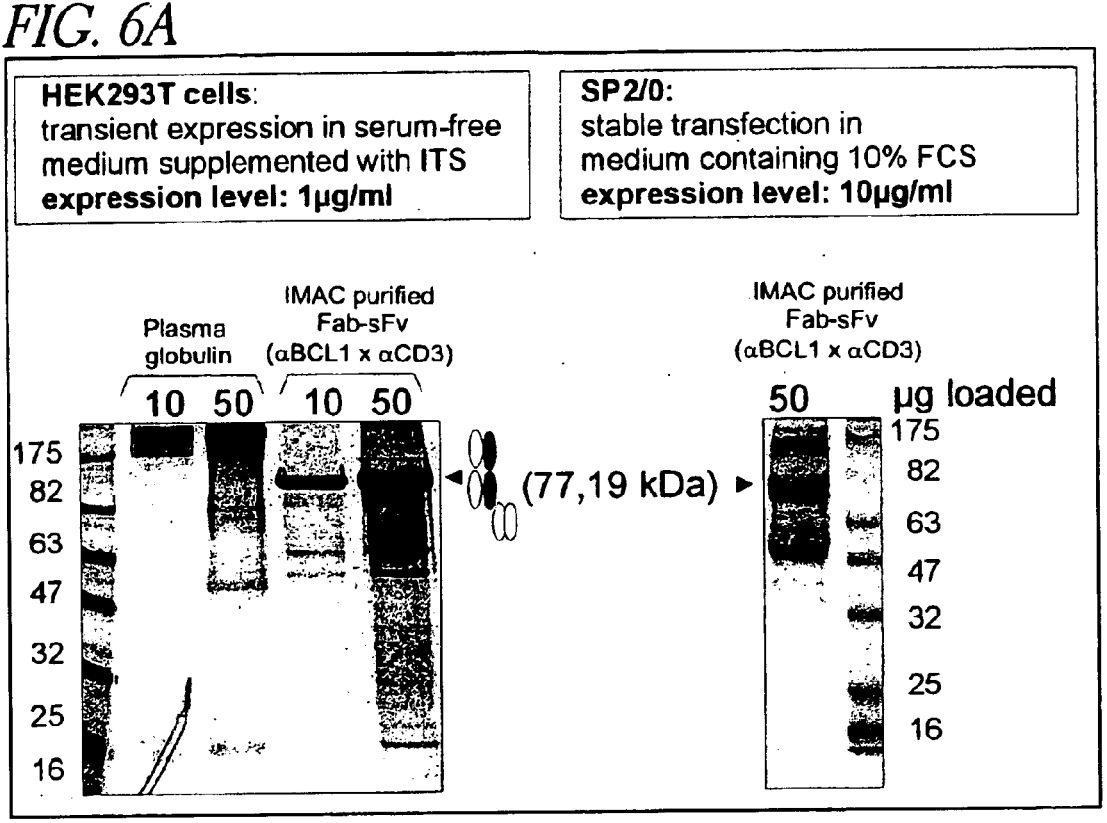
FIG. 6: Expression, functionality purification and serum stability of bispecific Fab-scFv molecules with Fab chains.
Figure 6B:
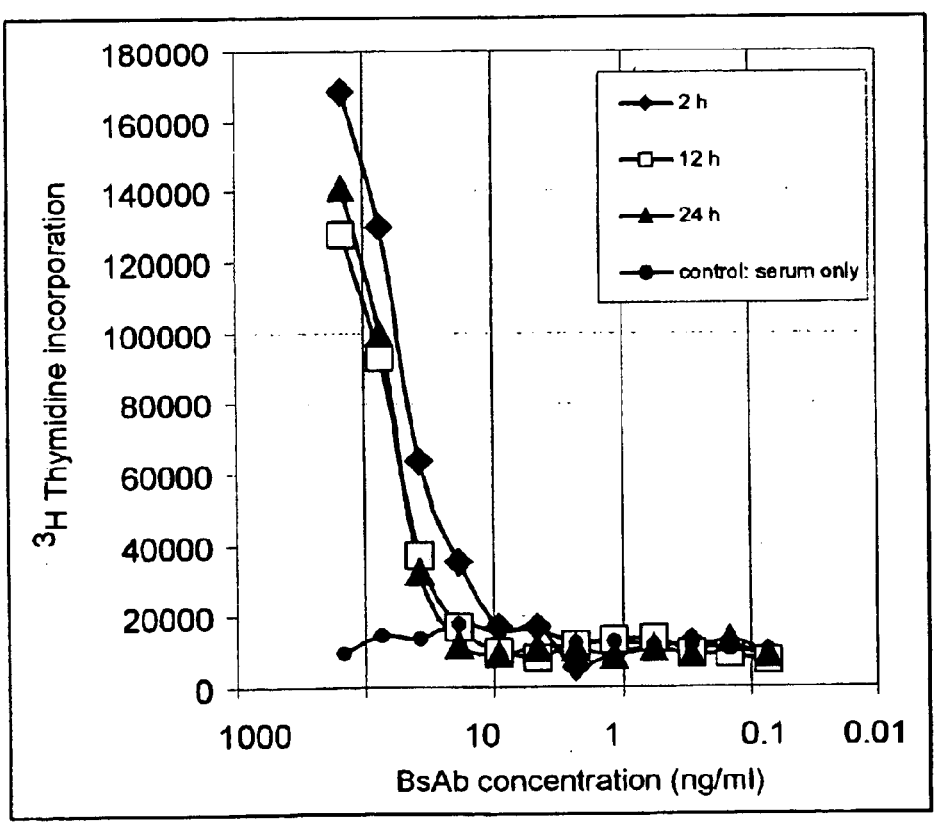

Fusing a second functionality to the Fd chain has the additional advantage that affinity purification targeted towards the Fd-scFv fusion (e.g. by inclusion of a His-tag in the molecule) removes the remaining non-functional L-chains. As mentioned, Fd:Fd homodimers never occur, so every Fd-chain or Fd-containing fusion protein is paired only with an L-chain or an L-chain derivative and are therefore in the bispecific format. Due to the efficient heterodimerization of the Fd and the L chain, the main heterologous product formed by transient or stable transformed cell lines is the desired product. FIG. 6A shows that the BsAb can be efficiently expressed in a transiently transformed HEK293T cell line (1 $\mu$g/ml culture medium) and in a stable transformed SP2/0 defective myeloid cell line (up to 10 $\mu$g/ml culture medium). After one-step affinity purification a 70–90% pure BsAb preparation could be obtained, depending whether the medium contained FCS or not. The purified BsAb was still active in a T-cell proliferation assay (data not shown). Incubation for up to 24 h in fresh serum derived from mouse did not result in a significant loss in activity (<30%), again measured by a T-cell proliferation assay (FIG. 6B).

FIG. 3 shows the expression of C-terminal Fab-scFv fusion proteins. The model of the BsAb intended by co-expression of two chains is schematically represented. Filled rectangles represent light chain derived domains, open rectangles heavy chain derived domains. 145-2C11derived domains are hatched The BsAbs were created by fusing the E6 ($\alpha$hPLAP) Fab fragment to either the 2c11 ($\alpha$CD3) or the 3D5 ($\alpha$HIS) scFv molecules. Different linker sequences were used to fuse the scFv to the C-terminus of either the L-chain (L2, 4, 5, 6, 7 and 8) or the Fd-chain (H1 and 2), ranging from 4 to 20 amino acids long. The amino acid composition is depicted with a single letter code. The pictures are from protein blots after non-reducing 10% SDS-PAGE of HEK 293T supernatant (harvested 24 h after transfection). The position of molecular weight markers is indicated beside the gel (M).

A] Co-transformation of the L and Fd-scFv expressing vectors result in a high degree of L:L homodimers and relative few Fab-scFv heterodimer (D1). Reversal of the orientation of the scFv (VHVL instead of VLVH) however resulted in more than 90% specific heterodimerization, with few contaminants of unpaired or homodimerized L-chains (D2), while keeping the connecting linker sequence. Essentially the same results were obtained when the interconnecting linker sequence was enlarged to 20 amino acids (D3), or when the scFv was fused to the C-terminus of the L-chain. The blots were probed with goat anti-mouse IgG γ/κ serum and revealed with an anti goat alkaline-phosphatase conjugated serum and NBT/BCIP.

B] Expression of a BsAb formed by coupling an anti-His scFv, also in a VLVH format, to the E6L-chain molecule using five different linker sequences. Immunodetection of the blotted proteins by anti mouse IgG γ/κ and anti E-tag shows that all detectable immunoglobulin molecules are in the expected heterodimer format. The first blot was revealed with hPLAP, showing the functionality of the E6Fab part of the molecule.

In FIG. 4 it is shown that the C-terminal Fab-scFv fusion proteins are functional as bispecific antibodies.

A] Functional cell binding of the Fab-H2-scFv (αhPLAPxαCD3) BsAb was demonstrated by flow cytometry on hPLAP-expressing fibrosarcoma cells (MO4I4) and on CD3 expressing T cells (TE2). The cells were incubated with the secondary detection antibody anti-mouse (Fab')$_2$-FITC (open curves) or pre-treated with the bispecific E6Fab-scFv and subsequently incubated with the detection antibody (filled curves). The bispecific Fab-scFv showed binding both to CD3$^+$ cells and to hPLAP$^+$ cells with satisfactory affinity.

B] Functional cell-cell ligation through the Fab-scFv was demonstrated by T-cell activation upon cross-linking of CD3. The first assay measures T-cell proliferation as a respons to the bridging of tumorcells and spleen cells mediated by the Fab-scFv BsAb (αhPLAPxαCD3) protein. For the hPLAP tumor model mitomycin treated MO4I4 cells were cocultured with C3H spleen cells (target/responder ration: 1/20). The non-hPLAP binding Fab-scFv BsAb (αBCL1xαCD3) protein was used as a control. T-cell proliferation was measured by tritium incorporation and depends on the concentration of the bispecific Fab-scFv.

The second assay measures the killing of the MO4I4 target cells by BsAb retargeted cytotoxic T-cells. A diagram is shown of the cytotoxic respons of alloreactive, syngenetic C3H spleen cells upon incubation with $^{51}$Cr labelled MO4I4 cells and in the presence of the proper bispecific Fab-scFv. The Fab-scFv BsAb (αhPLAPxαCD3) was able to bridge the effector cells to the target cells (cell ration 50/1) while the control Fab-scFv (αBCL1xαCD3) BsAb was not. Specific lysis was calculated by dividing the measured lysis minus the spontaneous lysis by the difference between the maximum lysis and the spontaneous lysis. Non-specific lysis was not over 10% of the maximal lysis.

In both assays, a specific T-cell activation could be noticed that was dependent on the presence of the hPLAP tumor antigen (data not shown), and on the presence and concentration of the Fab-scFv (αhPLAPxαCD3) BsAb.

FIG. 5 demonstrates that chimeric Fab molecules can be used to construct Fab-scFv bispecific antibodies.

A] Schematic representation of a Fab-scFv BsAb molecule containing chimeric Fab chains. In this example, the VH1 and VL1 domains are derived from the moAb B1, with an anti-BCL1 lymphoma specificity. The hybrid fusion molecule could efficiently be expressed in HEK293T cells as can be seen on the Western blot of a 10% non-reducing SDS-PAGE loaded with supernatant containing the molecules Fab-scFv (αBCL1xαCD3) BsAb (lane 1) or the control molecule bssFv (De Jonge et al; 1995). The detection system used is mentioned underneath each panel. The detected products and the molecular weight markers (kDa) are indicated.

The chimeric Fab-scFv (αBCL1xαCD3) BsAb retained binding specificity as shown by flow cytometry. Histograms are shown of flow cytometry analysis of BCL1$^{vitro}$ cells and TE2 CD3$^+$T-cells, incubated with the Fab-scFv (αBCL1xαCD3) BsAb and subsequently incubated with the detection antibody (filled curves) or incubated with the detection antibodies alone (open curves). Binding on the BCL1 B-cell lymphoma cells was detected by an anti HIS antibody (Qiagen, DE), followed by incubation with a goat anti mouse IgG1 serum and with a FITC-coupled anti goat serum. Binding to TE2 T-cells was demonstrated by incubation with the biotinylated ideotypic BCL1 IgM moAb followed by incubation with FITC-coupled streptavidin. The Fab-scFv (αBCL1xαCD3) BsAb showed binding to both CD3$^+$ cells and BCL1$^+$ cells with satisfactory affinity.

B] The chimeric Fab-scFv (αBCL1xαCD3) BsAb was proven to be active as a BsAb by antibody and target cell dependent activation of T cells, measured by proliferation and specific cytotoxicity assays. The curves show T-cell proliferation as a respons to the bridging of lymphoma cells and spleen cells mediated by the Fab-scFv (αBCL1xαCD3) BsAb protein. Mitomycin treated BCL1 cells were cocultured with Balb/c spleen cells in a target/responder ratio of 1/2. T-cell proliferation was measured by tritium incorporation and decreases with the dilution of the bispecific Fab-scFv. The diagram shows the cytotoxic respons of alloreactive, syngenetic Balb/c spleen cells upon incubation with $^{51}$Cr labelled BCL1$^{vitro}$ cells in the presence of the proper bispecific Fab-scFv. The αBCL1xαCD3 Fab-scFv is able to bridge the effector cells to the target cells (effector/target ratio 50/1) while the control BsAb with identical structure but a different specificity (αhPLAPxαCD3) was not.

FIG. 6 illustrates the expression, purification and serum-stability of bispecific Fab-scFv molecules (αBCL1xαCD3).

A] Immobilized metal affinity chromatography of bispecific Fab-scFv BsAb (αBCL1xαCD3). The culture medium of transiently (HEK293T) or stable (SP2/0) transfected cells was loaded on a NTA-Ni$^{2+}$ chelating column, eluted with imidazol and analyzed on a non-reducing 10% SDS-PAGE gel and stained with Coomassie Brilliant Blue (CBB). The purified Fab-scFv fractions were loaded in high amounts (10 and 50 μg) to enable the detection of small contaminating bands. For reference, standard plasma globulin (Sigma) was also loaded in the same quantities. The position of the Fab-scFv BsAb and its molecular weight is indicated. Molecular weight markers (kDa) are indicated on the side of the gel.

B] Serum stability of a Fab-scFv (αBCL1xαCD3). Purified BsAb fractions were incubated for up to 24 h in freshly isolated mouse serum. After incubation, the fractions were compared for their biological activity in a T-cell proliferation assay. Balb/c spleen cells were co-cultivated with mitomycin treated BCL1$^{vitro}$ cells in the presence of the bispecific B1Fab-scFv incubated in serum for 2, for 12 h or 24 h. Serum without bispecific B1Fab-scFv gave no response. There was no significant loss in activity of the bispecific Fab-scFv after 24 h of serum incubation.

EXAMPLE 3

Figure 7A:
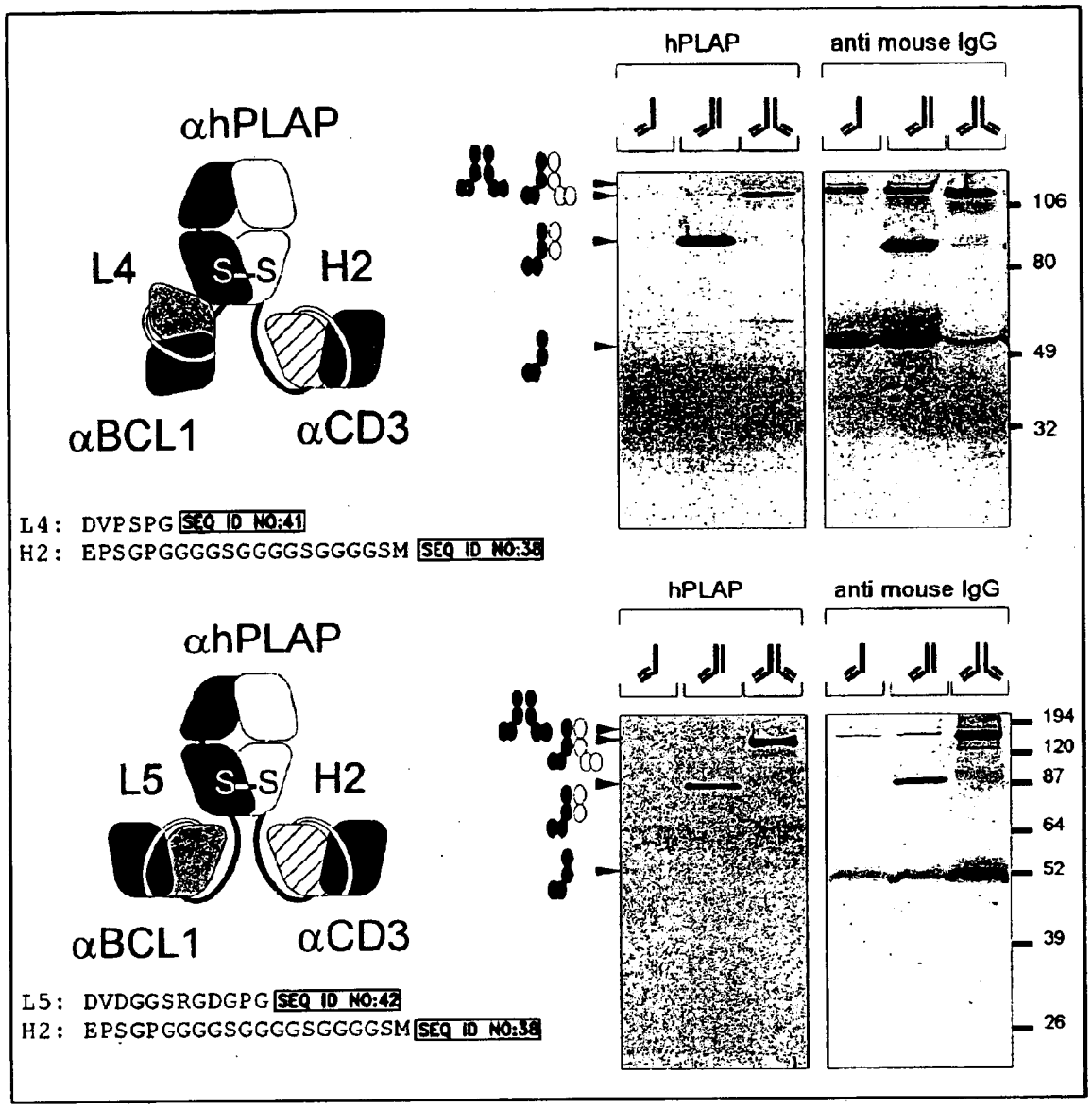
FIG. 7: Fd:L can efficiently heterodimerize two different scFv molecules.
Figure 7B:
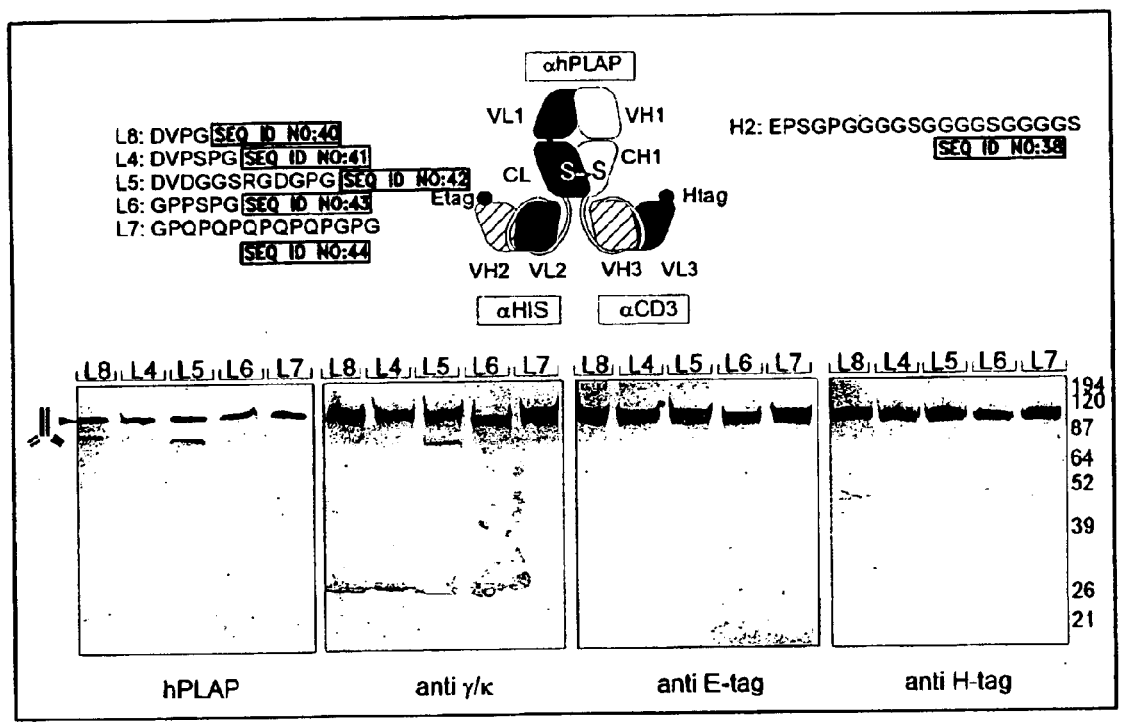
Figure 7C:
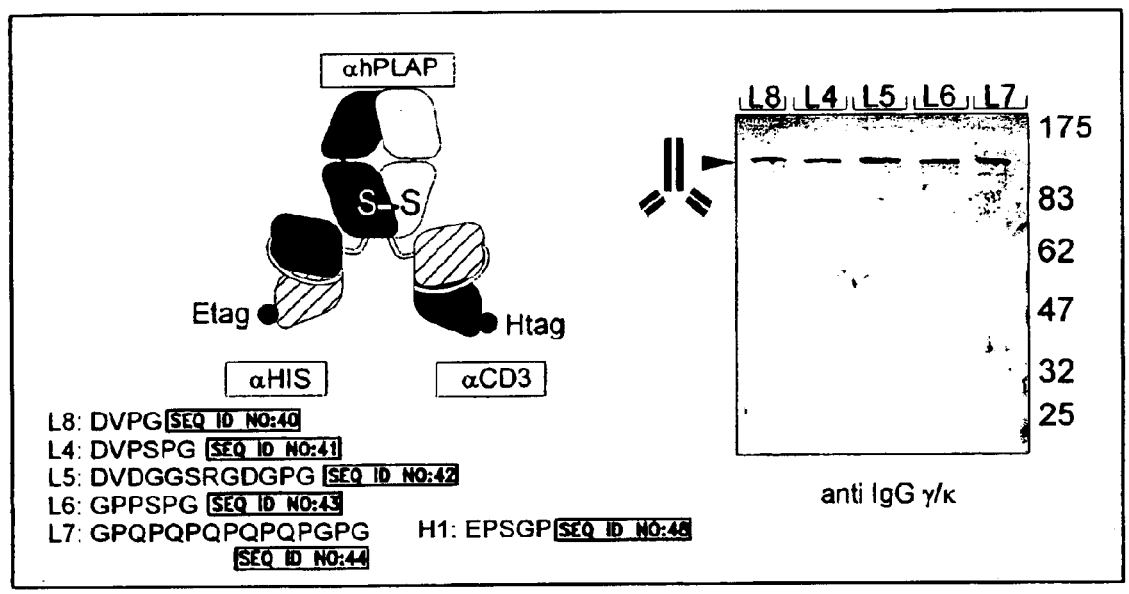
Figure 8A:
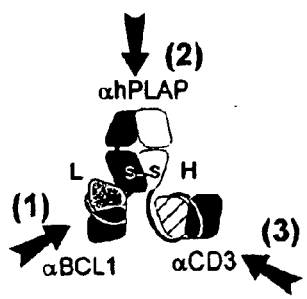
FIG. 8: Functionality of the trispecific antibody derivatives.
Figure 8A:
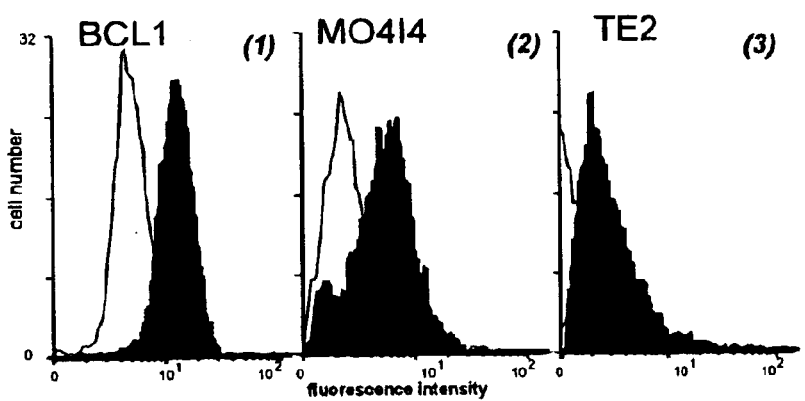
Figure 8B:
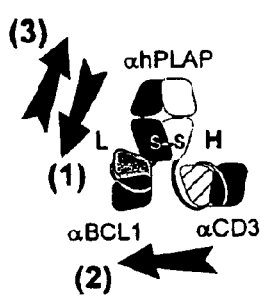
Figure 8B:
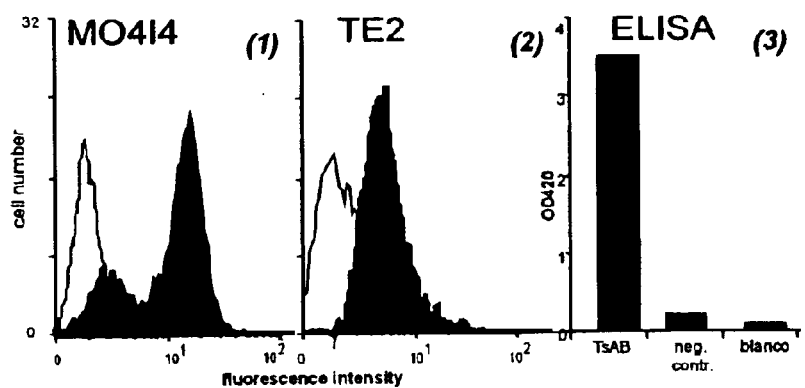
Figure 8C:
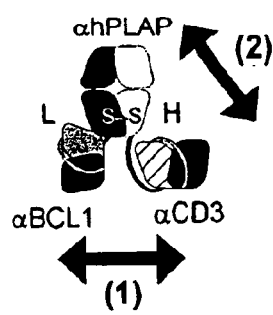
Figure 8C:
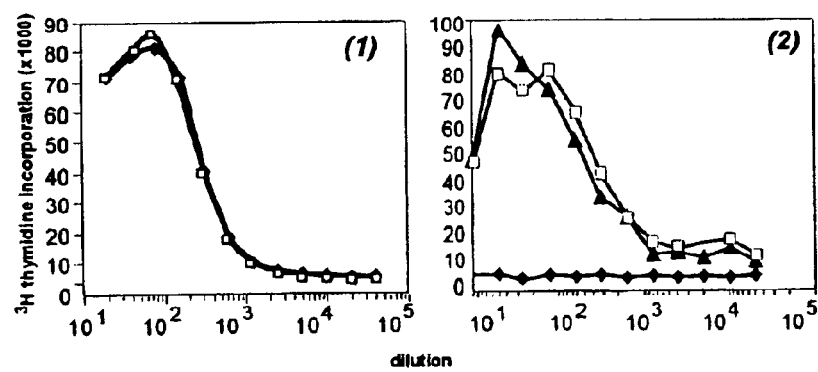

Fd:L Mediated Heterodimerization of Two Different scFv Molecules: Efficient Expression of Trispecific Antibodies Since C-terminal scFv fusion to either the Fd or the L chain could be expressed successfully and resulted in functional molecules, we investigated whether the Fab molecule could still be formed if both chains were elongated. When using the L:Fd heterodimerization signal to join two scFv molecules, a trispecific molecule can be created by also using the specificity of the Fab molecule created by the L:Fd heterodimerization. This was done by co-transfecting a VL-CL-VH2-VL2 (L-scFv) with a VH-CH1-VH3-VL3 (Fd-scFv) fusion-protein expressing vector (FIG. 7A). Especially when fusing two scFv molecules at the same side of the molecule it is important to monitor if binding functionality is not affected by the configuration of the TsAb. Fv domains have their antigen recognition side more oriented towards the N-terminal side, while this is also the side where the fusion to the Fab chains occur. Since the scFv molecules can be expected to direct their binding side more towards the Fab fragment, the possibility exists that by the 'crowding' by both the Fab and the second scFv, the binding to an antigen of the first scFv is hindered. From studies on linkers used in scFv molecules it is known that 15 amino acids are necessary to span the diameter of a Fv domain. Therefor we assume that such a linker would allow the scFv molecule to rotate its binding side away from the Fab. Furthermore, two single chain molecules could be hindering the normal interaction between the L:Fd pair and thus inhibit the heterodimerization of the TsAb. Therefore we constructed a series of molecules with varying peptide linkers connecting the Fab with the scFv molecules in two different TsAb models (FIG. 7A and 7B). Surprisingly, even the shorter linker sequences (4 amino acids) allowed efficient heterodimerization, and did not inhibit the function of the attached scFv molecules (FIG. 7 and 8). The TsAb (αhPLAP×αBCL1×αCD3) with a six amino acid linker connecting the αBCL1 scFv with the αhPLAP Fab and with a 20 amino acid linker connecting the αCD3 scFv with the Fab was further characterized. All binding specificities separately for cells expressing the appropriate marker could be demonstrated (FIG. 8A), as well as the simultaneous binding of one specificity to a (solid) support, while detecting via a second functional group (FIG. 8B). In order to show that the molecular design of the TsAb could allow the molecules to cross-link two antigens that were each fixed on the membranes of a different cell, we measured T-cell activation with a proliferation assay. Since the TsAb contain a binding site for two different tumor markers (hPLAP and BCL1) combined with an αCD3 specificity, the TsAb should be able to function in a proliferation assay with hPLAP-expressing cells as well as in a proliferation assay using BCL1 expressing cells. FIG. 8C shows that this is indeed the case: the TsAb (αhPLAP×αBCL1×αCD3) combines the activity of two separate BsAbs (αhPLAP×αCD3) and (αBCL1×αCD3), showing a simultaneous activity of the molecular parts along two crucial axes. Clearly, there was no problem of intramolecular crowding that inhibited the αBCL1scFv to bind even a lymphoma cell, while also attached to a T-cell via the second scFv.

Figure 9A:
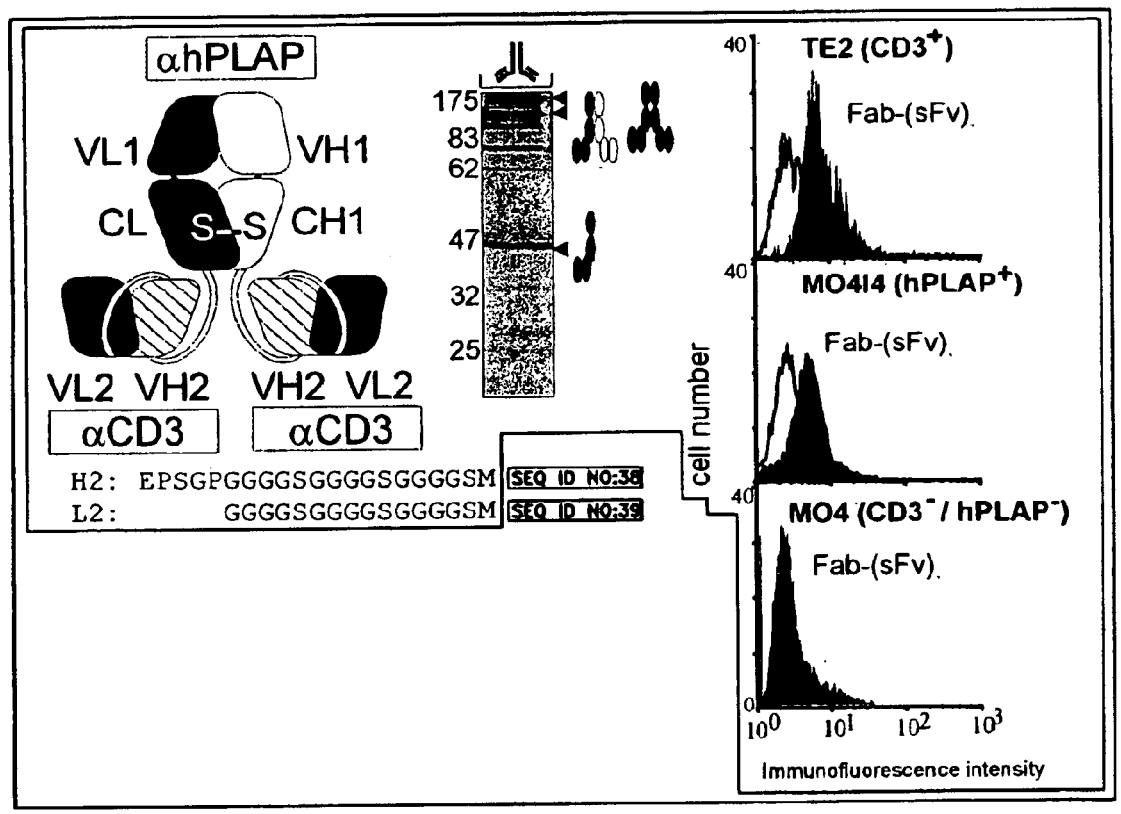
FIG. 9: Expression of multivalent antibody derivatives.
Figure 9B:
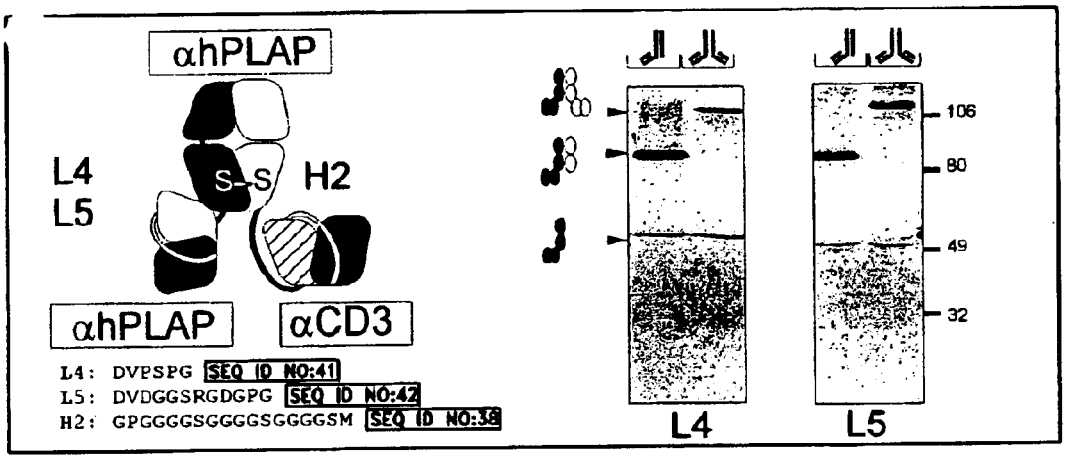
Figure 9C:
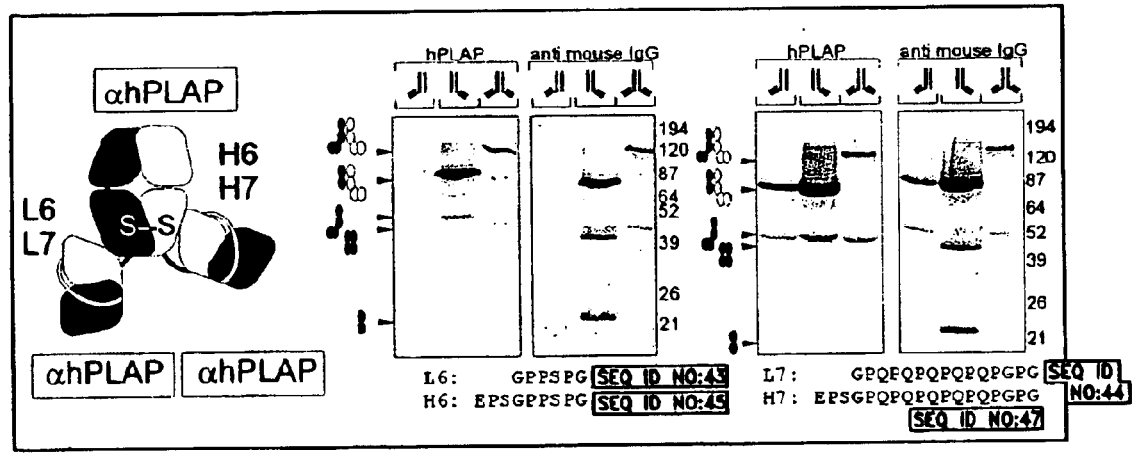

This molecule design allows free choice on the position of the binding sites and valence of the end product. A useful molecule with three functional groups could be a bispecific antibody targeting two different tumor antigens in stead of one (FIG. 7 and 8). A bivalent binding to the target cell receptor could be useful if the receptor is only triggered by forming larger aggregates and is insensitive to mere dimerization. In this case, the bivalent binding will accelerate the formation of aggregates at the target site (FIG. 9A). Otherwise, molecules with bivalent or multivalent binding to the target cell while keeping a monovalent binding for the triggering receptor on the effector cell could be useful to improve on the biodistribution of the antibody derivative (FIG. 9B). To improve on binding avidity, it is possible to create multivalent binding antibody derivatives with only one specificity (FIG. 9C). This design could be of importance in order to improve the avidity of molecules to be used for e.g. detection and diagnostics, in vitro as well as in vivo.

Figure 10:
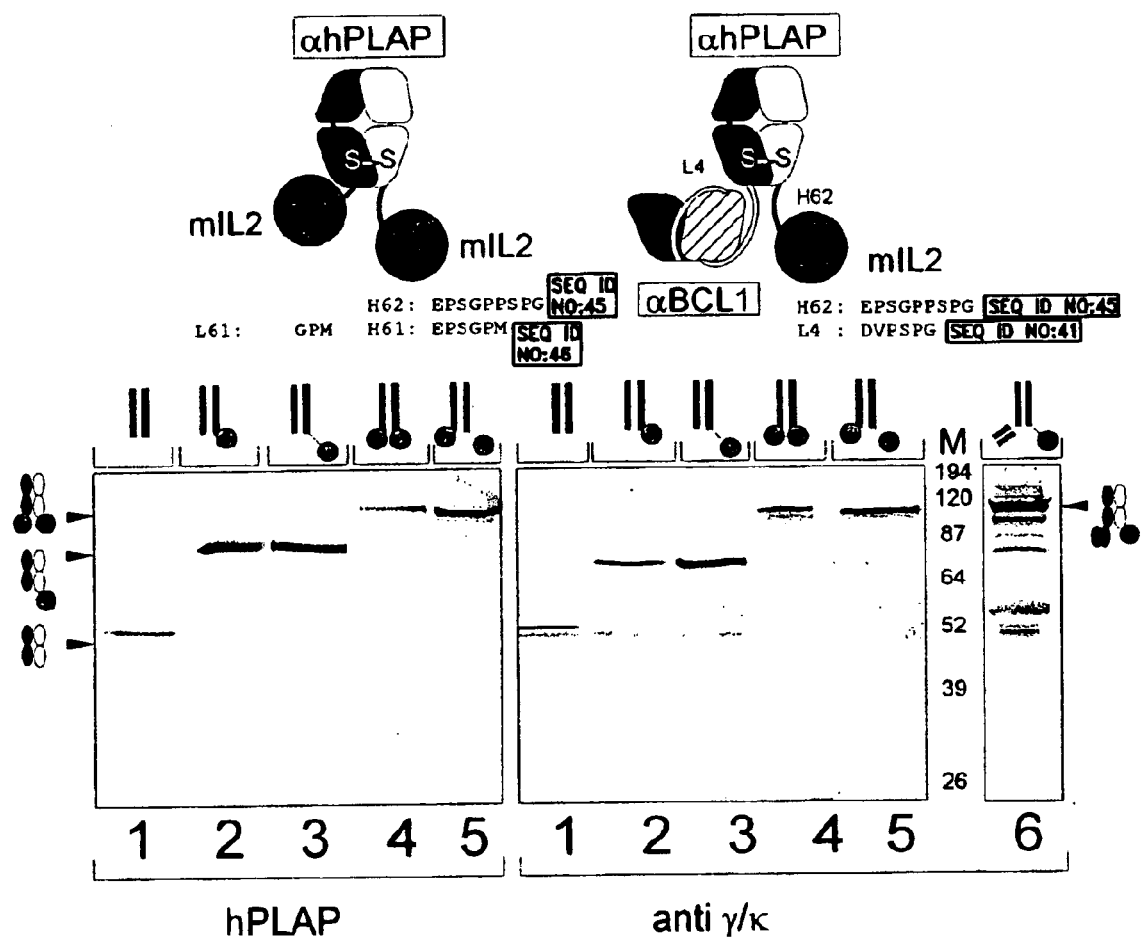
FIG. 10: Expression of multifunctional antibody derivatives.

The Fd and L chains can also be C-terminally extended with other molecules than scFv's. The targeting of certain signaling molecules to a predetermined cell type can be useful in therapeutic and diagnostic set up. We show that it is possible to use the L:Fd heterodimerization to associate two IL2 molecules, one fused to the L chain and another fused to the Fd chain, or to create a trifunctional molecule by fusing a scFv to one chain and a signalling molecule such as IL2 to another (FIG. 10).

FIG. 7 shows that Fd:L can efficiently heterodimerize two different scFv molecules.

A] Expression of trispecific antibodies that can target two different tumor antigens. The E6Fab chains were both extended at their C-terminal side with a ScFv molecule. An anti BCL1 tumor marker scFv was fused to the E6L chain using two different linker sequences: L4 and L5 of 6 and 12 amino acid length respectively. These fusion genes were co-expressed with an E6Fd-2c11 scFv (anti CD3 scFv) fusion with an interconnecting linker of 20 amino acids (linker H2). The gels show the medium of cells expressing the L-scFv alone or in combination with a non-extended Fd chain or with an Fd-scFv fusion. The arrows indicate the position of the L-scFv fusion monomer and dimer, and of the scFv-L:Fd and scFv-L:Fd-scFv heterodimer. All mouse immunoglobulin products were visualized by probing the blot with goat anti mouse IgG γ/κ. The hPLAP developed blot reveals functional hPLAP binding molecules (only E6L:Fd associations bind hPLAP). The position of the molecular weight markers is indicated on the side of the gel. Both TsAb molecules were efficiently produced.

B] Influence of linker composition and length on the production of trispecific antibody derivatives. An anti (H1S)$_6$ SCFV carrying an E-tag was coupled to the E6L chain using five different linker sequences, indicated as L4, L5, L6, L7 and LS. This E-tagged (αHIS) scFv-L fusion was combined with a HIS-tagged Fd-scFv (αCD3) and almost exclusively produced scFv-L:Fd-scFv heterodimers as shown by the revelation of the blotted proteins by hPLAP, anti IgG γ/κ, anti E-tag and anti HIS-tag. The position of the TsAb and of the molecular weight markers is shown on the side of the gel. All linker combinations gave equal expression levels of the TsAb.

C] In an analogous way, the L-chain with TLS, L4, L5, L6 and L7 linked αHISscFv could be heterodimerized with the Fd chain with a H1 coupled αCB3scFv. Especially important is the efficient expression of the L-(L8)-scFv with the Fd-(H1)-scFv, since both linkers are relatively short.

FIG. 8 demonstrates the functionality of the trispecific antibody derivatives.

The TsAb (αhPLAP×αBCL1×αCD3) with the L4 linker was produced to monitor its binding specificities and functionality.

A] All three encoded binding specificities are functional. The TsAb was shown to bind at (1) BCL1 B-cell lyphoma cells (BCL1$^+$), (2) MO4I4 fibrosarcoma cells (hPLAP$^+$) and (3) to the TE2 T-cell line (CD$^+$). Binding was detected by goat anti mouse serum γ/κ followed by an incubation with FITC-coupled anti goat serum.

B] The trispecific antibody derivative is able to bind two different molecules at the same time. While one antigen was fixed on a support (a cell membrane or plastic), a second specificity was used to detect the binding. The TsAb was bound to (1) MO$_4$I$_4$ (hPLAP$^+$) cells or (2) to TE2 T-cells, and subsequently incubated with biotinylated BCL1 IgM antibody (BCL1 is an idiotypic antigen) and FITC-coupled streptavidin. In a third setup BCL1 IgM was coated on MaxiSorb (Nunc) ELISA plates and detected by revealing the bound hPLAP (3). A (αhPLAP×αhPLAP×αCD3) antibody of the same configuration but lacking the αBCL1 specificity was used as a negative control. Blanco values were obtained by incubation with the detection antibodies alone (both with FACScan analysis and with ELISA experiments).

C] The trispecific antibody derivatives can cross-link two different cell markers. The TsAb (αhPLAP×αBCL1×αCD3) was able to act as efficiently as a BsAb in a T-cell proliferation assay with MO4I4 (hPLAP$^+$) cells and in an assay with BCL1 lymphoma cells as targets. This proves that the molecule acts as a bispecific antibody on both the (αhPLAP×CD3) and the (αBCL1×αCD3) axes. In this assay, both the TsAb with the L$_4$ and the L$_5$ linkers connecting the αBCL1 scFv to the L chain were compared.

(1) T-cell proliferation of Balb/c spleen cells upon cocultivation with mitomycin treated BCL1$^{vitro}$ cells in the presence of the trispecific antibody with linker 4 (TsAb (L4), or with linker 5 TsBab (L5). The linker length between the αCD3 and αBCL1 scFv and the Fab as no influence on the bridging capacity of the trispecific antibody.

(2) T-cell proliferation of C3H spleen cells upon cocultivation with mitomycin treated MO4I4cells in the presence of the trispecific antibody with linker 4 TsAb (L4) or with linker 5 TsBab (LS). The control B1Fab-sFb bispecific molecule does not induce T-cell proliferation. The linker length between the αBCL1 scFv and the Fab has no influence on the bridging capacity of the two other specificities in the trispecific antibody.

FIG. 9 illustrates the expression of multivalent antibody derivatives. Using the model of extending one or both of the L- or Fd chain of a Fab chain at their C-terminus with scFv molecules can lead to:

A] expression of bivalent T-cell binding bispecific antibody derivatives;

B] expression of bivalent tumor cell binding bispecific antibody derivatives; and C] expression of trivalent tumor cell binding monospecific antibody derivatives. 10% non-reducing SDS gels were blotted and developed with goat anti mouse IgG γ/κ followed by alkaline phosphatase coupled anti goat and NBT/BCIP staining, except when indicated that a hPLAP staining was performed. The FACScan-analysis was performed with the same antibodies, except the last detection antibody was a FITC-coupled anti goat serum. The position of the various antibody forms produced and of the molecular weight markers is shown at the side of the gels. All derivatives were produced in HEK293T cells by transient co-transformation of vectors expressing the indicated L-chain or Fd-chain fusion proteins. The linker sequences used fuse the scFv to the L or the Fd chain are indicated as L2, L4, L5, L6, L7, H2, H6 and H7 with single code amino acid sequences. The chains for which the expression vectors were co-transfected are drawn on top of the lanes.

In FIG. 10 the expression of multifunctional antibody derivatives is shown. The L:Fd interaction can be used to heterodimerize molecules of different classes. Here, fusion molecules of IL2 with both the L- or the Fd-chain were successfully expressed. This could even be accomplished when using a 3 amino acid linker for fusing to the L chain (L61), combined with a 6 amino acid linker for fusing to the Fd-chain (H61). The position of the fusion products after non-reducing 10% SDS-PAGE was revealed after protein blotting and immunodetection and is indicated beside the gel, as well as the position of the molecular weight markers run on the gel.

Different combinations of native L- and Fd-chains were co-expressed with complementary chains that were extended at their C-terminus with murine IL2 molecules or with a scFv molecule. Native L:Fd chains were combined (lane 1), as well as L:Fd-(H61)-mIL2 (lane 2), L:Fd-(H62)-mIL2 (lane 3), L-(L61)-mIL2:Fd-(H6l)-mIL2 (lane 4), L-(62)-mIL2:Fd-(H62)-mIL2 (lane 5) and L-(L4)-αBCL1scFv:Fd-(L62)-mIL2 (lane 6). The first gel was developed with hPLAP, gels 2 and 3 were developed with goat anti mouse IgG γ/κ followed by alkaline phosphatase coupled anti goat and NBT/BCIP staining.

This example shows that also signaling molecules (which can be different or alike) can be dimerized by the L:Fd interaction, without loss of binding activity of the reconstituted Fab fragment. Also molecules belonging to different molecular classes, such as signaling molecules and scFv molecules, can be heterodimerized by the L:Fd interaction.

In summary, the present invention relates to a class of molecules specified as novel multipurpose antibody derivatives. This class of molecules is created by heterodimerization of two constituting components. Heterodimerization is obtained by the specific heterotypic interaction of a chosen VH-CH1 combination of immunoglobulin domains, with a chosen VL-CL combination of immunoglobulin domains. The VHCH1-VLCL interaction is proposed as a very efficient heterodimerization scaffold that could be efficiently produced. By choosing the appropriate VH and VL domains in the VHCH1 and VLCL context, a binding specificity can be constituted by the heterodimerization scaffold itself. One or both of the comprising VHCH1 and VLCL chains can thus be extended at either the N- or the C-terminus or both with other molecules, for the purpose of combining these molecules with each other.

The other molecules that are genetically coupled to the heterodimerization scaffold with peptide linkers of choice, can be a toxin polypeptide, an enzyme, a hormone, a cytokine, a signaling molecule, or a single chain linked Fv fragment with the same or a different specificity. In this way, combining three or more different specificities by combining a Fab molecule with a certain specificity with two or more scFv molecules with two or more different specificities can lead to trispecific or multispecific antibodies derivatives while maintaining a lower molecular weight.

Also, the method described allows for the production of bispecific antibodies with a bivalent binding of only one specificity, while maintaining a monovalent binding of the other specificity. In its minimal form, the methods allows for the creation of bispecific antibodies with monovalent binding to each antigen, by combining a specificity encoded by the Fab chains with a single scFv fusion, without the inclusion of a linker sequence derived from an immunoglobulin hinge region.

This format differs from previously described gene-engineered antibody formats by using the intrinsic behavior of the Fab-chain fragments to heterodimerize. One or more extensions can be made at the N- or C-terminal side, but never including a hinge region, which by itself is a homodimerizing motif. By not including the hinge region, it is much simpler to obtain monovalent binding specificities in the molecule.

Deposit Data

The following deposits were made pursuant to rule 28 EPC:
1. pCAGGSE6L (present in *E. coli* MC1061λ cells deposited on Oct. 15, 1997 at the Belgian Coordinated Collection of Microorganisms and given the deposit accession no. LMBP3714)
2. pCA2C11sFvE6Hf (present in *E. coli* DH5α cells deposited on Oct. 15, 1997 at the Belgian Coordinated Collection of Microorganisms and given the deposit accession no. LMBP3715)
3. pCAE6HfGS2C11sFv (also identified as pCAE6H2sc2C11H) (present in *E.coli* MC1061 cells deposited on Oct. 15, 1997 at the Belgian Coordinated Collection of Microorganisms and given th deposit accession no. LMBP3716)

ABBREVIATIONS

| | |
|---|---|
| Ab | antibody |
| BME | β-mercaptoethanol |
| BsAb | bispecific antibody |
| BssFv | bispecific single chain Fv fragment |
| BSA | bovine serum albumin |
| BvAb | bivalent antibody |
| C- | carbon-terminus |
| ° C. | degrees Celsius |
| 2C11 | from 145-2C11 hamster anti CD3 antibody |
| CD3(ε) | cluster of differentiation 3 (ε-chain) |
| CH1, CH3 | first and third constant domain of the immunoglobulin heavy chain |
| CL | constant domain of the immunoglobulin light chain |
| COS-1 | CV-1 cells with defective SV40 origin of replication |
| DNA | desoxyribonucleic acid |
| DMEM | Dulbecco minimal essential medium |
| EDTA | ethylenediaminetetraacetic acid |
| E6 | murine monoclonal antibody against hPLAP |
| *E. coli* | *Escherichia coli* |
| f | fragment |
| Fab | antigen binding fragment including VL, CL, VH and CH1 |
| Fab' | Fab fragment with hinge region |
| FACS | Fluorescence activated cell sorter |
| Fc | fragment with C-terminal domains of the immunoglobulin heavy chain |
| FCS | Foetal calf serum |
| Fd | VH-CH1 heavy chain fragment, truncated after CH1 |
| FITC | fluorescein isothiocyanate |
| γ | Ig heavy chain |
| h | hours |
| H | Ig heavy chain |
| HEK | human embryonic kidney cells |
| hPLAP | human placental alkaline phosphatase |
| Ig | immunoglobulin |
| IL2 | interleukin 2 |
| IMAC | immobilized metal affinity chromatography |
| kDa | kilodalton |
| κ | Ig light chain |
| l | linker sequence |
| L | light chain |
| LB | Luria-Bertani |
| LMBP | Laboratory of Molecular Biology Plasmid Collection |
| M | molar |

-continued
ABBREVIATIONS

| | |
|---|---|
| min | minutes |
| mpAb | multipurpose antibody |
| N- | amino-terminus |
| NP-40 | nonidet-P40 |
| PAGE | polyacrylamide gel electrophoresis |
| PBS | phosphate buffered saline |
| PCR | polymerase chain reaction |
| rpm | revolution(s) per minute |
| SDS | sodium dodecyl sulfate |
| sec | second |
| sFv | single-chain linked Fv-fragment |
| SV40 | simian virus 40 |
| TE | Tris-EDTA-buffer |
| U | unit |
| UTR | untranslated region |
| VH, VL | variable domains of the Ig heavy and light chains |
| 3D5 | from the scFv 3D5 specific for $(His)_6$ |
| mIL2 | mouse interleukin 2 |
| Bla | *Escherichia coli* Beta-lactamase |
| H1-7 | linker peptide in the heavy chain derived fusion products |
| L1-8 | linker peptide in the light chain derived fusion products |
| B1 | hamster mAb against BCL1 idiotype |
| IDA | International Depositary Authority LMBP/BCCM Plasmid Collection, K. L. Ledeganckstraat 35, B-9000 Gent |
| CTL | cytotoxic T-lymphocyte |
| (Fab')$_2$ | dimerized Fab' fragments |
| $^3$H | tritium |
| $^{51}$Cr | radioactive chromium |
| α | anti |
| CBB | Coomassie Brilliant Blue |
| VH2 | VH domain derived from the second antibody |
| VL2 | VL domain derived from the second antibody |
| VH3 | VH domain derived from the third antibody |
| VL3 | VL domain derived from the third antibody |

REFERENCES

Carter P., Kelley R. F., Rodrigues M. L., Snedecor B., Covarrubias M., Velligan M. D., Wong W. L. T., Rowland A. M., Kotts C. E., Carver M. E., Yang M., Bourell J. H., Shepard H. M. and Hennes D. (1992) High level *Escherichia coli* expression and production of a bivalent humanized antibody fragment. Bio/Technology 10, 163–167.

Cheung S. C., Dietzschold B., Koprowski H., Notkins A. L. and Rando R. F. (1992) A recombinant human Fab expressed in *Escherichia coli* neutralizes Rabies virus. J. Virol. 66(11), 3714–6720.

Choe, M., Webber K. O. & Pastan I. (1994)-B3(Fab)-PE38M: a recombinant immunotoxin in which a mutant form of Pseudomonas exotoxin is fused to the Fab fragment of monoclonal antibody B3. Cancer Res 54 (13), 3460–3467.

Coloma M. J. and Morrison, S. L. (1997) Design and production of novel tetravalent bispecific antibodies. Nat. Biotech. 15, 159–163.

De Jonge J., Brissinck J., Heirman, C., Demanet C., Leo O., Moser M. and Thielemans K. (1995) Production and characterization of bispecific single-chain antibody fragments. Mol. Immunol. 17(18), 1405–1412.

De Butter K., Feys V., Van de Voorde A. and Fiers W. (1992a) Production of functionally active murine and murine::human chimeric F(ab')2 fragments in COS-1 cells. Gene 113, 223–230.

De Butter K., Remaut E., & Fiers, W. (1992b) Disulphide bridge formation in the periplasm of *E. coli*:β-lactamase: Human IgG3 hinge fusion as a model system. Mol. Microbiol. 6, 2201–2208.

De Waele P., Feys V., Van de Voorde A., Molemans F. and Fiers W. (1988) Expression in non-lymphoid cells of mouse recombinant immunoglobulin directed against the tumor marker human placental alkaline phosphatase. Eur. J. Biochem. 176, 287–295.

DuBridg R. B., Tang P., Hsia H. C., Leong P-M., Miller J. H. and Calos M. P. (1987) Analysis of mutations in human cells by using an Epstein-Barr virus shuttle system. Mol. Cell. Bial. 7, 379–387.

Ducancel F., Gillet D., Carrier A., Lajeunesse E., Ménez A. & Boulain J.C. (1993)—Recombinant colorimetric antibodies:construction and characterization of a bifunctional F(ab)2/Alkaline Phosphatase conjugate roduced in *Escherichia coli*. Bio/Technology 11, 601–605

Flamez D., Remaut E. and Fiers W. (1995.) Production in *Escherichia coli* of a functional murine and murine::human F(ab')2 fragment and mature antibody directed against human placental alkaline phosphatase. J. Biotechnol. 42, 133–143.

Grooten J. and Fiers W. (1989) Acquisition by the. murine host of responsiveness towards various neoplastic cell lines, but not towards self, through adoptive transfer of a helper T lymphocyte clone with anti self specificity. Cancer Res. 49(14), 3872–3878.

Hendrix P. G., Dauwe S. E., Van de Voorde A., Nouwen E. J., Hoylaerts M. F. and De Broe M. (1991) Radiolocalisation and imaging of stably hPLAP-transfected $Mo_4$ tumours with monoclonal antibodies and fragments. Br. J. Cancer 64, 1060–1068.

Holliger P., Prospero T. and Winter G. (1993) 'Diabodies': Small bivalent and bispecific antibody fragments. Proc. Nat. Acad. Sci. USA 90, 6444–6448.

Hu S., Shivily L., Raubitschek A., Sherman M., Williams L. E., Wong J. Y. C., Shivily E. J. and Wu A. M. (1996) Minibody: A Novel engineered anti carcino-embryonic antigen antibody fragment (single-chain Fv-CH3) which exhibits rapid high-level targeting of xenografts. Cancer Res. 56, 3055–3061.

Huylebroeck D., Maertens G., Verhoeyen M., Lopez C., Raeymakers A., Min Jou W. and Fiers W. (1988) High-level transient expression of influenza virus proteins from a series of SV40 late and early replacement vectors. Gene 66, 163–181.

Jost C. R., Kurucz I., Jacobus C. M., Titus J. A., George A. J. T. and Segal D. M. (1994) Mammalian expression and secretion of functional Single-Chain Fv molecules. J. Biol. Chem. 269(42), 26267–26273.

Knappick, A. & Plückthun, A. (1994) An improved affinity tag based on the FLAG peptide for the detection and purification of recombinant antibody fragments. Biotechniques 17(4), 754–761.

Laemali U. K. (1970) Cleavage of structural proteins during the assembly of the head of bacteriophage T4, Nature 227, 680–685.

Lammerant W., (1994–1995) Produktie van antilichamen, antilichaamderivaten en recombinante immunotoxines in *Saccharomyces cerevisiae*. Rijksuniversiteit Gent, PhD. Thesis.

Leo O., Foo M., Sachs D. H., Samelson L. E. and Bluestone J. A. (1987) Identification of a monoclonal antibody specific for a murine T3 polypeptide. Proc. Natal. Acad. Sci. USA 84(S), 1374–1378.

Mertens, N., Remaut, E. And Fiers, W. (1995) Versatile, multi-featured plasmids for high-level expression of heterologous genes in *Escherichia coli*: overproduction of human and murine cytokine. Gene 164, 1–15.

Nina H., Yamamura K. and Miyazaki J. (1991) Efficient selection for high-expression transfectants with a novel eukaryotic vector. Gene 108, 193–200.

Ridgway J. B. B., Presta L. G. And Carter P. (1996) 'Knobs-into-holes' engineering of CH3 domains for heavy chain heterodimerization. Prot. Eng. 9(7), 617–621.

Smans K. A., Hoylaerts M. F., Narisawa S., Millán J. L. And De Broe M. E. (1995) Bispecific antibody-mediated lysis of placental and germ cell alkaline phosphatase targeted solid tumors in immunocompetent mice. Cancer Res. 55, 4383–4390.

Ward, E. S. Expression and purification of antibody fragments using *E. coli* as a host. (1992). In: Antibody engineering, a practical guide. Editor: C. A. K. Borrebaeck. Publisher: W. H. Freemand and co, New York.

What is claimed is:

1. A multipurpose heterodimeric antibody derivative, comprising CL and VL domains interacting with CH1 and VH domains, said antibody derivative further comprising two or more other molecules having at least one further purpose coupled to two or more of said domains by a peptide bond at a C-terminus of the heterodimeric antibody, and wherein the heterodimerization is driven by the heterotypic interaction between the CH1-VH combination and the CL-VL combination of immunoglobulin domains.

2. The multipurpose heterodimeric antibody derivative according to claim 1 wherein at least a first of the two or more other molecules is coupled to the CH1-VH chain and at least a second of the two or more other molecules is coupled to the CL-VL chain.

3. The multipurpose heterodimeric antibody derivative according to claim 1 wherein the two or more other molecules are selected from the group consisting of: sFv molecules, toxins, enzymes, hormones, cytokine and signaling molecules.

4. The multipurpose heterodimeric antibody derivative according to claim 1, wherein the coupling of two or more of said domains to the other molecules takes place via a linker.

5. The multipurpose heterodimeric antibody derivative according to claim 4, wherein the linker is an amino acid chain of at least 1 amino acid.

6. The multipurpose heterodimeric antibody derivative according to claim 1 wherein a first other molecule is coupled to the C-terminal side of the CH1 domain and a second other molecule is coupled to the C-terminal side of the CL domain.

7. The multipurpose heterodimeric antibody derivative according to claim 6 wherein an sFv molecule is coupled to each of said CH1 and CL domains.

8. The multipurpose heterodimeric antibody derivative according to claim 1 wherein said antibody is a multivalent antibody.

9. The multipurpose heterodimeric antibody derivative according to claim 1 wherein said antibody is a bispecific antibody.

10. The multipurpose heterodimeric antibody derivative according to claim 1 wherein said antibody is a trispecific antibody.

11. The multipurpose heterodimeric antibody derivative according to claim 1 wherein said antibody is a multispecific antibody.

12. A pharmaceutical preparation comprising the multipurpose antibody derivative of claim 1 and a pharmaceutically acceptable diluent.

13. A diagnostic preparation comprising multipurpose heterodimeric antibodies according to claim 1.

14. A multipurpose heterodimeric antibody derivative, comprising CL and VL domains interacting with CH1 and VH domains, wherein said CH1 domain is not linked to a hinge region, said antibody derivative further comprising two or more other molecules having at least one further purpose coupled to two or more of said domains by a peptide bond at a C-terminus of the heterodimeric antibody, and wherein the heterodimerization is driven by the heterotypic interaction between the CH1-VH combination and the CL-VL combination of immunoglobulin domains.

15. A multipurpose heterodimeric antibody derivative according to claim 14, wherein the two or more other molecules are selected from the group consisting of: sFv molecules, toxins, enzymes, hormones, cytokine and signaling molecules.

16. A multipurpose heterodimeric antibody derivative, comprising CL and VL domains interacting with CH1 and VH domains, wherein said CH1 domain is not linked to a hinge region, said antibody derivative further comprising two or more other molecules having at least one further purpose coupled to two or more of said domains, wherein a first sFv molecule is coupled to the C-terminal side of the CH1 domain and a second sFv molecule is coupled to the C-terminal side of the CL domain, and wherein the heterodimerization is driven by the heterotypic interaction between the CH1-VH combination and the CL-VL combination of immunoglobulin domains.

* * * * *

UNITED STATES PATENT AND TRADEMARK OFFICE
CERTIFICATE OF CORRECTION

PATENT NO. : 6,809,185 B1
DATED : October 26, 2004
INVENTOR(S) : Schoonjans et al.

It is certified that error appears in the above-identified patent and that said Letters Patent is hereby corrected as shown below:

Column 1,
Lines 2-3, "International Application PCT/EP99/00447" should be changed to
-- International Application PCT/EP99/00477 --.

Column 45,
Line 40, "enzymes, hormones, cytokine" should be changed to -- enzymes, hormones, cytokines --.

Column 46,
Line 47, "enzymes, hormones, cytokine" should be changed to -- enzymes, hormones, cytokines --.

Signed and Sealed this

Twenty-ninth Day of November, 2005

JON W. DUDAS
*Director of the United States Patent and Trademark Office*

SEQUENCE LISTING

```
<160> NUMBER OF SEQ ID NOS: 48

<210> SEQ ID NO 1
<211> LENGTH: 26
<212> TYPE: DNA
<213> ORGANISM: Artificial Sequence
<220> FEATURE:
<223> OTHER INFORMATION: Polynucleotide linker

<400> SEQUENCE: 1
ccgtctcctc agagctccaa aaaccc                                          26

<210> SEQ ID NO 2
<211> LENGTH: 20
<212> TYPE: DNA
<213> ORGANISM: Artificial Sequence
<220> FEATURE:
<223> OTHER INFORMATION: CH1 domain forward primer

<400> SEQUENCE: 2
```
cactgccgag ctcccaaaac					20

<210> SEQ ID NO 3
<211> LENGTH: 21
<212> TYPE: DNA
<213> ORGANISM: Artificial Sequence
<220> FEATURE:
<223> OTHER INFORMATION: CH1 domain reverse primer

<400> SEQUENCE: 3
tcatgtcgcg gccgcgctct a					21

<210> SEQ ID NO 4
<211> LENGTH: 14
<212> TYPE: PRT
<213> ORGANISM: Artificial Sequence
<220> FEATURE:
<223> OTHER INFORMATION: Amino acid linker 1

<400> SEQUENCE: 4

Val Asn His Lys Pro Ser Asn Thr Lys Val Asp Lys Arg Val
 1               5                  10

<210> SEQ ID NO 5
<211> LENGTH: 28
<212> TYPE: DNA
<213> ORGANISM: Artificial Sequence
<220> FEATURE:
<223> OTHER INFORMATION: 2 C11scFv forward primer

<400> SEQUENCE: 5
ggcccatgga ggtcaagctg gtggagtc					28

<210> SEQ ID NO 6
<211> LENGTH: 43
<212> TYPE: DNA
<213> ORGANISM: Artificial Sequence
<220> FEATURE:
<223> OTHER INFORMATION: 2 C11scFv reverse primer

<400> SEQUENCE: 6
ataggatcct tatccggacc ttttatttcc agcttggtgc cag					43

<210> SEQ ID NO 7
<211> LENGTH: 21
<212> TYPE: DNA
<213> ORGANISM: Artificial Sequence
<220> FEATURE:
<223> OTHER INFORMATION: Fd fragment forward primer

<400> SEQUENCE: 7
gctgaaaggg cccggtggag g					21

<210> SEQ ID NO 8
<211> LENGTH: 29
<212> TYPE: DNA
<213> ORGANISM: Artificial Sequence
<220> FEATURE:
<223> OTHER INFORMATION: Fd fragment reverse primer

<400> SEQUENCE: 8
ggtcccaggg cactggcctc actctagag					29

<210> SEQ ID NO 9
<211> LENGTH: 21

```
<212> TYPE: DNA
<213> ORGANISM: Artificial Sequence
<220> FEATURE:
<223> OTHER INFORMATION: CL forward primer

<400> SEQUENCE: 9
cagtgagcag ttaacatctg g                                              21

<210> SEQ ID NO 10
<211> LENGTH: 23
<212> TYPE: DNA
<213> ORGANISM: Artificial Sequence
<220> FEATURE:
<223> OTHER INFORMATION: CL reverse primer

<400> SEQUENCE: 10
cctttggggc ccacactcat tcc                                            23

<210> SEQ ID NO 11
<211> LENGTH: 21
<212> TYPE: DNA
<213> ORGANISM: Artificial Sequence
<220> FEATURE:
<223> OTHER INFORMATION: forward primer

<400> SEQUENCE: 11
gctgaaaggg cccggtggag g                                              21

<210> SEQ ID NO 12
<211> LENGTH: 30
<212> TYPE: DNA
<213> ORGANISM: Artificial Sequence
<220> FEATURE:
<223> OTHER INFORMATION: reverse primer

<400> SEQUENCE: 12
gtgccagggc actggttaag atctggatcc                                     30

<210> SEQ ID NO 13
<211> LENGTH: 24
<212> TYPE: DNA
<213> ORGANISM: Artificial Sequence
<220> FEATURE:
<223> OTHER INFORMATION: B1VH domain forward primer

<400> SEQUENCE: 13
cctcacctcg agtgatcagc actg                                           24

<210> SEQ ID NO 14
<211> LENGTH: 21
<212> TYPE: DNA
<213> ORGANISM: Artificial Sequence
<220> FEATURE:
<223> OTHER INFORMATION: B1VH domain reverse primer

<400> SEQUENCE: 14
ccacctgagg agacagtgac c                                              21

<210> SEQ ID NO 15
<211> LENGTH: 26
<212> TYPE: DNA
<213> ORGANISM: Artificial Sequence
<220> FEATURE:
<223> OTHER INFORMATION: forward primer

<400> SEQUENCE: 15
```
ctgcctcctc aggcaaaaca acaccc                                              26

<210> SEQ ID NO 16
<211> LENGTH: 22
<212> TYPE: DNA
<213> ORGANISM: Artificial Sequence
<220> FEATURE:
<223> OTHER INFORMATION: reverse primer

<400> SEQUENCE: 16
ggacccagtg catgccatag cc                                                  22

<210> SEQ ID NO 17
<211> LENGTH: 21
<212> TYPE: DNA
<213> ORGANISM: Artificial Sequence
<220> FEATURE:
<223> OTHER INFORMATION: VL(B1) sequence forward primer

<400> SEQUENCE: 17
ggatgtgaca ttgtgatgac c                                                   21

<210> SEQ ID NO 18
<211> LENGTH: 18
<212> TYPE: DNA
<213> ORGANISM: Artificial Sequence
<220> FEATURE:
<223> OTHER INFORMATION: VL(B1) sequence reverse primer

<400> SEQUENCE: 18
gatcctttga gctccagc                                                       18

<210> SEQ ID NO 19
<211> LENGTH: 20
<212> TYPE: DNA
<213> ORGANISM: Artificial Sequence
<220> FEATURE:
<223> OTHER INFORMATION: CL(E6) sequence forward primer

<400> SEQUENCE: 19
gttggagctc aaacgggctg                                                     20

<210> SEQ ID NO 20
<211> LENGTH: 26
<212> TYPE: DNA
<213> ORGANISM: Artificial Sequence
<220> FEATURE:
<223> OTHER INFORMATION: CL(E6) sequence reverse primer

<400> SEQUENCE: 20
ggagctggtg gtggcgtctc aggacc                                              26

<210> SEQ ID NO 21
<211> LENGTH: 36
<212> TYPE: DNA
<213> ORGANISM: Artificial Sequence
<220> FEATURE:
<223> OTHER INFORMATION: E6L sequence forward primer

<400> SEQUENCE: 21
ataccgctcg agacacagac atgagtgtgc ccactc                                   36

<210> SEQ ID NO 22
<211> LENGTH: 51
<212> TYPE: DNA
<213> ORGANISM: Artificial Sequence -continued

```
<220> FEATURE:
<223> OTHER INFORMATION: E6L sequence reverse primer

<400> SEQUENCE: 22
cgcggatcct tacccgggga cgtcacactc attcctgttg aagctcttga c          51

<210> SEQ ID NO 23
<211> LENGTH: 31
<212> TYPE: DNA
<213> ORGANISM: Artificial Sequence
<220> FEATURE:
<223> OTHER INFORMATION: B1scFv forward primer

<400> SEQUENCE: 23
tcccccgggg aagtgaagct ggtggagtct g                                31

<210> SEQ ID NO 24
<211> LENGTH: 42
<212> TYPE: DNA
<213> ORGANISM: Artificial Sequence
<220> FEATURE:
<223> OTHER INFORMATION: B1scFv reverse primer

<400> SEQUENCE: 24
ataggatcct tatccggatt tcagctccag cttggtccca gc                    42

<210> SEQ ID NO 25
<211> LENGTH: 34
<212> TYPE: DNA
<213> ORGANISM: Artificial Sequence
<220> FEATURE:
<223> OTHER INFORMATION: E6scFv gene forward primer

<400> SEQUENCE: 25
tcccccgggc aggttcagct gcagcagtct ggag                             34

<210> SEQ ID NO 26
<211> LENGTH: 41
<212> TYPE: DNA
<213> ORGANISM: Artificial Sequence
<220> FEATURE:
<223> OTHER INFORMATION: E6scFv gene reverse primer

<400> SEQUENCE: 26
ataggatcct tatccggacc gttttatttc cagcttggtc c                     41

<210> SEQ ID NO 27
<211> LENGTH: 26
<212> TYPE: DNA
<213> ORGANISM: Artificial Sequence
<220> FEATURE:
<223> OTHER INFORMATION: Adaptor oligonucleotide

<400> SEQUENCE: 27
cgacggtggt tctagaggtg atgggc                                      26

<210> SEQ ID NO 28
<211> LENGTH: 34
<212> TYPE: DNA
<213> ORGANISM: Artificial Sequence
<220> FEATURE:
<223> OTHER INFORMATION: Adaptor oligonucleotide

<400> SEQUENCE: 28
ccgggcccat cacctctaga accaccgtcg acgt                             34
```

-continued

<210> SEQ ID NO 29
<211> LENGTH: 39
<212> TYPE: DNA
<213> ORGANISM: Artificial Sequence
<220> FEATURE:
<223> OTHER INFORMATION: oligonucleotide

<400> SEQUENCE: 29
ggcctcaacc acaacctcag ccgcaacctc aacctgggc                    39

<210> SEQ ID NO 30
<211> LENGTH: 39
<212> TYPE: DNA
<213> ORGANISM: Artificial Sequence
<220> FEATURE:
<223> OTHER INFORMATION: oligonucleotide

<400> SEQUENCE: 30
ccgggcccag gttgaggttg cggctgaggt tgtggttga                    39

<210> SEQ ID NO 31
<211> LENGTH: 39
<212> TYPE: DNA
<213> ORGANISM: Artificial Sequence
<220> FEATURE:
<223> OTHER INFORMATION: Oligonucleotide in vector PCDE6H7scE6

<400> SEQUENCE: 31
ggcctcaacc acaacctcag ccgcaacctc aacctgggc                    39

<210> SEQ ID NO 32
<211> LENGTH: 39
<212> TYPE: DNA
<213> ORGANISM: Artificial Sequence
<220> FEATURE:
<223> OTHER INFORMATION: Oligonucleotide in vector PCDE6H7scE6

<400> SEQUENCE: 32
ccgggcccag gttgaggttg cggctgaggt tgtggttga                    39

<210> SEQ ID NO 33
<211> LENGTH: 34
<212> TYPE: DNA
<213> ORGANISM: Artificial Sequence
<220> FEATURE:
<223> OTHER INFORMATION: 3D5scFv forward primer

<400> SEQUENCE: 33
tcccccgggg acattttgat gacccaaact ccac                         34

<210> SEQ ID NO 34
<211> LENGTH: 44
<212> TYPE: DNA
<213> ORGANISM: Artificial Sequence
<220> FEATURE:
<223> OTHER INFORMATION: 3D5scFv reverse primer

<400> SEQUENCE: 34
ataggatcct tatccggatt cggcccccga ggccgcagag acag               44

<210> SEQ ID NO 35
<211> LENGTH: 57
<212> TYPE: DNA
<213> ORGANISM: Artificial Sequence
<220> FEATURE:
<223> OTHER INFORMATION: E-tag coding sequence -continued

```
<400> SEQUENCE: 35
tccggagcgc cggtgccgta tccagatccg ctggaaccac gtggcgccta aggatcc        57

<210> SEQ ID NO 36
<211> LENGTH: 16
<212> TYPE: PRT
<213> ORGANISM: Artificial Sequence
<220> FEATURE:
<223> OTHER INFORMATION: Amino acid linker

<400> SEQUENCE: 36

Val Asn His Lys Pro Ser Asn Thr Lys Val Asp Lys Arg Val Glu Leu
 1               5                  10                  15

<210> SEQ ID NO 37
<211> LENGTH: 4
<212> TYPE: PRT
<213> ORGANISM: Artificial Sequence
<220> FEATURE:
<223> OTHER INFORMATION: Amino acid linker

<400> SEQUENCE: 37

Glu Pro Ser Gly
 1

<210> SEQ ID NO 38
<211> LENGTH: 21
<212> TYPE: PRT
<213> ORGANISM: Artificial Sequence
<220> FEATURE:
<223> OTHER INFORMATION: Amino acid linker H2

<400> SEQUENCE: 38

Glu Pro Ser Gly Pro Gly Gly Gly Ser Gly Gly Gly Ser Gly
 1               5                  10                  15

Gly Gly Gly Ser Met
                20

<210> SEQ ID NO 39
<211> LENGTH: 16
<212> TYPE: PRT
<213> ORGANISM: Artificial Sequence
<220> FEATURE:
<223> OTHER INFORMATION: Amino acid linker L2

<400> SEQUENCE: 39

Gly Gly Gly Gly Ser Gly Gly Gly Gly Ser Gly Gly Gly Gly Ser Met
 1               5                  10                  15

<210> SEQ ID NO 40
<211> LENGTH: 4
<212> TYPE: PRT
<213> ORGANISM: Artificial Sequence
<220> FEATURE:
<223> OTHER INFORMATION: Amino acid linker L8

<400> SEQUENCE: 40

Asp Val Pro Gly
 1

<210> SEQ ID NO 41
<211> LENGTH: 6
<212> TYPE: PRT
<213> ORGANISM: Artificial Sequence
<220> FEATURE:
```

<223> OTHER INFORMATION: Amino acid linker L4

<400> SEQUENCE: 41

Asp Val Pro Ser Pro Gly
 1               5

<210> SEQ ID NO 42
<211> LENGTH: 12
<212> TYPE: PRT
<213> ORGANISM: Artificial Sequence
<220> FEATURE:
<223> OTHER INFORMATION: Amino acid linker L5

<400> SEQUENCE: 42

Asp Val Asp Gly Gly Ser Arg Gly Asp Gly Pro Gly
 1               5                  10

<210> SEQ ID NO 43
<211> LENGTH: 6
<212> TYPE: PRT
<213> ORGANISM: Artificial Sequence
<220> FEATURE:
<223> OTHER INFORMATION: Amino acid linker L6

<400> SEQUENCE: 43

Gly Pro Pro Ser Pro Gly
 1               5

<210> SEQ ID NO 44
<211> LENGTH: 15
<212> TYPE: PRT
<213> ORGANISM: Artificial Sequence
<220> FEATURE:
<223> OTHER INFORMATION: Amino acid linker L7

<400> SEQUENCE: 44

Gly Pro Gln Pro Gln Pro Gln Pro Gln Pro Gln Pro Gly Pro Gly
 1               5                  10                  15

<210> SEQ ID NO 45
<211> LENGTH: 9
<212> TYPE: PRT
<213> ORGANISM: Artificial Sequence
<220> FEATURE:
<223> OTHER INFORMATION: Amino acid linker H6 (also H62)

<400> SEQUENCE: 45

Glu Pro Ser Gly Pro Pro Ser Pro Gly
 1               5

<210> SEQ ID NO 46
<211> LENGTH: 6
<212> TYPE: PRT
<213> ORGANISM: Artificial Sequence
<220> FEATURE:
<223> OTHER INFORMATION: Amino acid linker H61

<400> SEQUENCE: 46

Glu Pro Ser Gly Pro Met
 1               5

<210> SEQ ID NO 47
<211> LENGTH: 18
<212> TYPE: PRT
<213> ORGANISM: Artificial Sequence
<220> FEATURE:
<223> OTHER INFORMATION: Amino acid linker H7

```
<400> SEQUENCE: 47

Glu Pro Ser Gly Pro Gln Pro Gln Pro Gln Pro Gln Pro Gln Pro Gly
1               5                   10                  15

Pro Gly

<210> SEQ ID NO 48
<211> LENGTH: 5
<212> TYPE: PRT
<213> ORGANISM: Artificial Sequence
<220> FEATURE:
<223> OTHER INFORMATION: Amino acid linker H1

<400> SEQUENCE: 48

Glu Pro Ser Gly Pro
1               5
```